United States Patent [19]

Hagenah et al.

[11] Patent Number: 4,846,873
[45] Date of Patent: Jul. 11, 1989

[54] 1-CARBOALKOXYALKYL-3-ALKOXY-4-(2'-CARBOXYPHENYL)-AZET-2-ONES AS PLANT GROWTH REGULATORS AND SELECTIVE HERBICIDES

[75] Inventors: Jeffrey A. Hagenah, Greenbrae; Ahmad Omid, Walnut Creek, both of Calif.

[73] Assignee: Chevron Research Company, San Francisco, Calif.

[21] Appl. No.: 53,310

[22] Filed: May 22, 1987

Related U.S. Application Data

[63] Continuation-in-part of Ser. No. 867,115, May 23, 1986, abandoned, and Ser. No. 867,353, May 23, 1986, abandoned.

[51] Int. Cl.[4] .................... A01N 43/44; C07D 205/08
[52] U.S. Cl. ........................ 71/88; 540/360; 540/354
[58] Field of Search .................. 71/88; 540/360, 354

[56] References Cited

U.S. PATENT DOCUMENTS 4,479,900 10/1984 Luo ..................................... 540/360

Primary Examiner—Mark L. Berch
Attorney, Agent, or Firm—S. R. La Paglia; R. C. Gaffney; L. S. Squires

[57] ABSTRACT

Compounds of the formula:

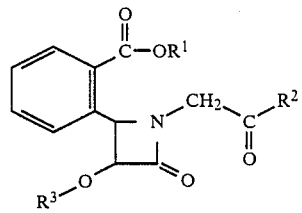

wherein $R^1$ is lower alkyl of 1 to 6 carbon atoms lower alkenyl of 2 to 6 carbon atoms or benzyl; $R^2$ is lower alkoxy of 1 to 6 carbon atoms, benzyloxy or the group

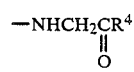

where $R^4$ is lower alkoxy of 1 to 4 carbon atoms; and $R^3$ is hydrogen, lower alkyl of 1 to 6 carbon atoms, lower alkyl of 1 to 6 carbon atoms substituted with 1 to 3 trihalomethyl groups, lower haloalkyl of 1 to 6 carbon atoms substituted with 1 to 6 halogen atoms, lower alkenyl of 2 to 6 carbon atoms, arylalkyl of 7 to 12 carbon atoms, lower alkoxyalkyl of 2 to 6 carbon atoms, lower alkylthioalkyl of 2 to 6 carbon atoms, or lower cycloalkyl of 3 to 8 carbon atoms are active as plant growth regulators. Certain of these compounds also show activity as selective herbicides.

60 Claims, No Drawings

1-CARBOALKOXYALKYL-3-ALKOXY-4-(2'-CARBOXYPHENYL)-AZET-2-ONES AS PLANT GROWTH REGULATORS AND SELECTIVE HERBICIDES

CROSS-REFERENCE TO RELATED APPLICATIONS

This application is a continuation-in-part of U.S. Ser. No. 867,115 ABN and U.S. Ser. No. 867,353 ABN, both filed May 23, 1986.

BACKGROUND OF THE INVENTION

The present invention relates to 1-carboalkoxyalkyl-3-alkoxy-4-(2'-carboxyphenyl)-azet-2-ones and their activities as plant growth regulators, and to the activities of some of those compounds as selective herbicides.

The commonly assigned U.S. Pat. No. 4,456,467 of Francis J. Freenor III discloses compounds of the formula:

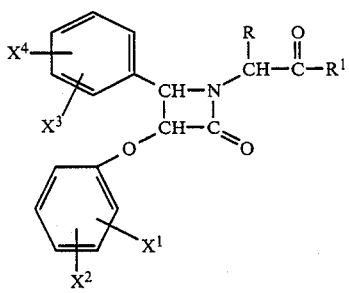

wherein R is hydrogen or alkyl of 1 to 3 carbon atoms; $R^1$ is hydrogen, alkyl of 1 to 6 carbon atoms, alkoxy of 1 to 6 carbon atoms, alkylthio of 1 to 6 carbon atoms or $NR^1R^2$ wherein $R^1$ and $R^2$ are independently hydrogen or alkyl of 1 to 12 carbon atoms; and $X^1$, $X^2$, $X^3$ and $X^4$ are independently hydrogen, chloro, bromo, fluoro, iodo, alkyl of 1 to 4 carbon atoms or alkoxy of 1 to 4 carbon atoms, which are active as plant growth regulators.

The commonly assigned U.S. Pat. No. 4,443,372 of Tatao Luo, Louis Russo and Francis J. Freenor III discloses 1-lower alkyl derivatives of 3-aryloxy-4-(2-carbalkoxy)-phenyl-azet-2-one compounds of the formula:

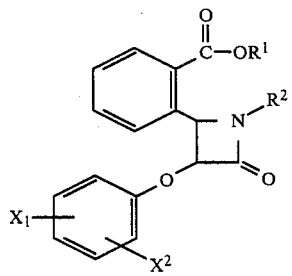

wherein $R^1$ is methyl or ethyl; $R^2$ is lower alkyl; and $X_1$ and $X_2$ are independently hydrogen or halogen which are active as plant growth regulators.

The commonly-assigned U.S. Pat. No. 4,479,900 of Tatao Luo discloses compounds of the formula:

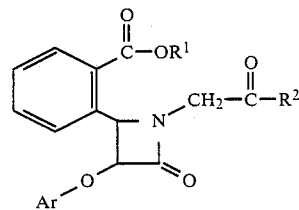

wherein $R^1$ is lower alkyl or benzyl; $R^2$ is lower alkoxy, benzyloxy or the group

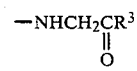

wherein $R^3$ is lower alkoxy and Ar is phenyl optionally substituted with 1 to 3 substituents independently selected from halogen, trihalomethyl, nitro, and lower alkyl which show plant growth regulating activity.

The commonly-assigned U.S. Pat. No. 4,620,867 of Tatao Luo discloses compounds of the formula:

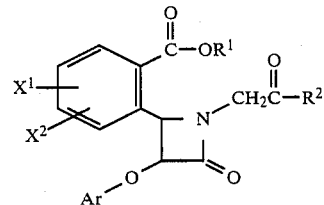

wherein $R^1$ is lower alkyl or benzyl; $R^2$ is lower alkoxy, benzyloxy or the group

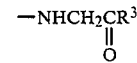

where $R^3$ is lower alkoxy; Ar is phenyl or phenyl substituted with 1 to 3 substituents independently selected from halogen, trihalomethyl, nitro, phenyl, lower alkoxy and lower alkyl; and $X^1$ and $X^2$ which are independently hydrogen, halogen, lower alkoxy, or lower alkyl, or $X^1$ and $X^2$ taken together form an aromatic ring fused with the phenyl ring, provided that both $X^1$ and $X^2$ are not hydrogen which show activity as plant growth regulators.

U.S. Pat. No. 4,181,800 discloses a large group of anti-microbial 2-azetidinone compounds of the general formula:

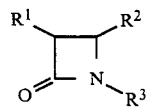

wherein $R^1$ is amino, substituted amino, substituted hydroxy, azido or halogen; $R^2$ is hydrogen, hydroxymethyl, aralkoxyaminomethyl, aryl, aralkenyl, formyl, carboxy, or a residue of a nucleophile; and $R^3$ is a group of the

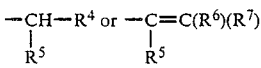

wherein $R^4$ is aryl, aralkyl, arylthioalkyl or a heterocyclic group; $R^5$ is carboxy or its derivative; $R^6$ is alkyl, haloalkyl, arylthio or heterocyclic-thioalkyl; and $R^7$ is hydrogen, haloalkyl or heterocyclic-thioalkyl; (subject to various provisos). The compounds are disclosed as useful antibiotics for treating microbial infections in mammals.

U.S. Pat. No. 4,207,234 discloses a large class of antimicrobial 4-unsubstituted acetidinone compounds which have the general formula:

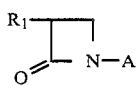

wherein $R^1$ is amino or acylamino; and A is hydrogen or the group:

wherein $R^x$ is hydrogen; $R^y$ is, in pertinent part, hydrogen or alkyl of up to 6 carbon atoms; and $R^2$ is, in pertinent part, carboxy, hydroxy, amino, cyano, or alkyl of up to 6 carbon atoms substituted by carboxy or a salt thereof. These compounds are disclosed as useful as antibiotics to treat microbial infections in mammals.

SUMMARY OF THE INVENTION

The plant growth regulating compounds of my invention are represented by the formula:

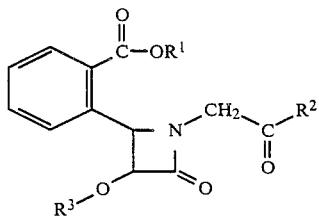

wherein $R^1$ is lower alkyl of 1 to 6 carbon atoms, lower alkenyl of 2 to 6 carbon atoms, or benzyl; $R^2$ is lower alkoxy of 1 to 6 carbon atoms, benzyloxy or the group

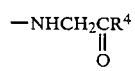

where $R^4$ is lower alkoxy of 1 to 6 carbon atoms; and $R^3$ is hydrogen, lower alkyl of 1 to 6 carbon atoms lower alkyl of 1 to 6 carbon atoms substituted with 1 to 3 trihalomethyl groups, lower haloalkyl of 1 to 6 carbon atoms substituted with 1 to 6 halogen atoms, lower alkenyl of 2 to 6 carbon atoms, arylalkyl of 7 to 12 carbon atoms, lower alkoxyalkylene of 2 to 6 carbon atoms, lower alkylthioalkylene of 2 to 6 carbon atoms, or lower cycloalkyl of 3 to 8 carbon atoms.

Among other factors, the present invention is based on my finding that these compounds exhibit surprising activity as plant growth regulators. In particular, use of these compounds in the treatment of plants may result in a saving of labor in the care of the plants, such as by decreasing the need for mowing turf or for physical pruning of fruit trees and ornamentals due to the compounds' herbistatic and chemical pruning activities. Use of these compounds may also increase the yield in plants such as cucumbers by increasing both flowering and the proportion of female flowers. These compounds may also increase the yield in commercially important crops, such as soybeans.

The plant growth regulating (PGR) activities of these compounds appear to be very susceptible to structural change, such that while the compounds of this invention having a carboalkoxy group in the ortho position on the 4-phenyl group show unexpectedly good PGR activity, corresponding compounds having the carboalkoxy groups in the meta or para position show significantly less PGR activity. It is believed that the trans isomer of these compounds, that is, where the 3-alkoxy and the 4-phenyl groups are in the trans position (configuration), has greater PGR activity than the corresponding cis isomer.

As is apparent from their structures, the compounds of Formula I have asymmetric carbon atoms and thus can exist as optical and geometric isomers. Accordingly, the respective optical isomers and geometric isomers, as well as mixtures thereof, are encompassed within the invention.

Preferred $R^1$ groups include methyl and ethyl.
Preferred $R^2$ groups include lower alkoxy and the group

wherein $R^4$ is lower alkoxy. Particularly preferred $R^2$ groups include methoxy and ethoxy. Especially preferred are compounds wherein $R^2$ is ethoxy.

Preferred $R^3$ groups include lower alkyl groups and lower haloalkyl groups. Particularly preferred lower alkyl $R^3$ groups include branched chain alkyl groups. Especially preferred branched-chain alkyl groups include those alkyl groups wherein said branching is on the carbon atom attached to the oxygen atom. Preferred haloalkyl groups include $\beta,\beta,\beta$-trihaloethyl, especially preferred is $\beta,\beta,\beta$-trifluoroethyl. Particularly preferred are those compounds wherein $R^3$ is $\beta,\beta,\beta$-trifluoroethyl, isopropyl or tert-butyl.

The compounds of the following formula:

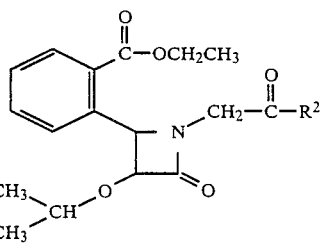

wherein $R^2$ is lower alkoxy of 1 to 6 carbon atoms, benzyloxy or the group

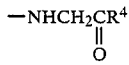

wherein R⁴ is lower alkoxy also show activity as selective herbicides.

The compounds of Formula IA show surprisingly good herbicidal activity against weeds and other undesired plants while being surprisingly safe on crops such as soybeans, cotton and alfalfa. This selectivity is particularly important since the above species constitute important food and feed crops and many herbicides which are active against weeds, particularly broad-leaved weeds, show phytotoxicity on these crops. Moreover, these compounds show surprising herbicidal selectivity and safety on soybeans when compared to other azet-2-ones which are active as plant growth regulators. (See, e.g., Tables. IV to XI.)

As with the plant growth regulating compounds of Formula I, it is believed that the trans isomer of these herbicidal compounds, that is, those compounds where the 3-isopropoxy and the 4-phenyl groups are in the trans position, has greater herbicidal activity than the corresponding cis isomer.

As is apparent, the compounds of Formula IA have asymmetric carbon atoms and thus can exist as optical and geometric isomers. Accordingly, the respective optical isomers and geometric isomers, as well as mixtures thereof, are encompassed within the invention.

Preferred herbicidal compounds include those where R² is lower alkoxy. Especially preferred R² groups include ethoxy, methoxy, n-propoxy, isopropoxy and the like.

Definitions

As used herein, the following terms have the following meanings, unless expressly stated to the contrary.

The term "alkyl" refers to both straight- and branched-chain alkyl groups. The term "lower alkyl" refers to both straight- and branched-chain groups having a total of from 1 to 6 carbon atoms and includes primary, secondary and tertiary alkyl groups. Typical lower alkyls include, for example, methyl, ethyl, n-propyl, isopropyl, and the like.

The term "halo" or "halogen" refers to the groups fluoro, chloro, bromo, and iodo.

The term "lower alkoxy" refers to the group OR' where R' is lower alkyl. Typical lower alkoxy groups include methoxy, ethoxy, and the like.

The term "carboalkoxy" refers to the group

where R' is an alkyl group. The term "lower carboalkoxy" refers to carboalkoxy groups where R' is a lower alkyl group. Typical carboalkoxy groups include carbomethoxy, carboethoxy, and the like.

The term "haloalkyl" refers to alkyl groups substituted with from 1 to 6 halogen atoms. "Lower haloalkyl" refers to haloalkyl groups having a total of from 1 to 6 carbon atoms, and includes, for example, β,β,β-trifluoromethyl; 1,1,1,3,3,3-hexafluoroisopropyl-, and the like.

The term "cycloalkyl" refers to cyclic alkyl groups. The term "lower cycloalkyl" refers to groups having from 3 to 8 carbon atoms in the ring and includes, for example, cyclopropyl, cyclohexyl, cyclopentyl, 1-methylcyclopropyl, and the like.

The term "alkylene" refers to straight- and branched-chain alkylene groups and includes groups of the formula —(CH₂)$_m$— wherein m is an integer greater than zero, as well as groups such as 2-methylpropylene [e.g.,

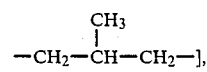

3-methylpentylene

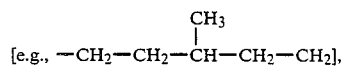

and the like. Thus, typical alkylene groups include methylene, ethylene, propylene, 2-methylbutylene, and the like.

The term "alkoxyalkyl" refers to the group R'OR"- wherein R' is alkyl and R" is alkylene. The term "lower alkoxyalkylene" refers to groups having a total of from 2 to 6 carbon atoms. Examples include methoxymethyl, ethoxymethyl, isopropoxyethyl, and the like.

The term "alkylthio" refers to the group R'S— wherein R' is alkyl. The term "lower alkythio" refers to alkylthio groups having 1 to 6 carbon atoms; examples include methylthio, ethylthio, n-hexylthio, and the like.

The term "alkylthioalkyl" refers to groups having the formula R'SR"—wherein R' is alkyl and R" is straight- or branched-chain alkylene. The term "lower alkylthioalkyl" refers to alkylthioalkyl groups wherein R' is lower alkyl and R" has a chain length of up to 6 carbon atoms. Typical lower alkylthioalkyl groups include ethylthioethyl, isopropylthiomethyl, isopropylthiobutyl, hexythioethyl, methylthiomethyl, ethylthiomethyl, methylthioethyl, and the like.

The term "alkenyl" refers to unsaturated aliphatic groups having at least one a double bond, [e.g., CH₃CH=CH(CH₂)₂—] and includes both straight- and branchedchain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methylpent-4-enyl, and the like.

The term "aryl" refers to aryl groups having from 6 to 12 carbon atoms and includes, for example, phenyl, naphthyl, indenyl, and the like. Typically, the aryl group will be phenyl or naphthyl, as compounds having such groups are more readily available commercially than other aryl compounds. The term "arylalkyl" refers to an alkyl group of 1 to 4 carbons substituted with an aryl group of from 6 to 12 carbons and includes, for example, benzyl, p-methylbenzyl and 2-phenylethyl.

As used herein, the term "trans" as it applies to the compounds of the present invention means:

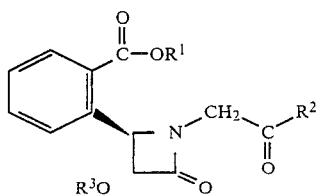

employing the three-dimensional bonding well known to the skilled artisan; whereas the term "cis", as it is used herein, means:

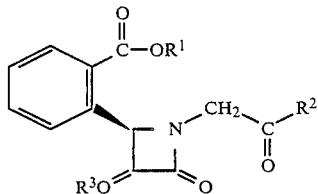

Examples of trans isomers include the compounds of Examples 15 to 18.

The terms "plant growth regulator" ("PGR") and "plant growth regulating" refer to compounds and/or their activities which alter growth or development of a plant such as by a direct or indirect effect on natural phytohormone systems which may result in a beneficial increase or decrease in growth rate of the entire plant or a specific plant organ, or by helping a plant to adjust to stress, such as by increased tolerance to drought, salt or wind. These growth regulating effects include, but are not limited to increased branching, bud break at nodes which do not normally produce branches; advanced or delayed, increased or decreased flowers and set of flowers; reduction of stem height; preventing or retarding the growth of lateral buds; the promotion of the thinning of superfluous fruits in various fruit trees; and inducing or breaking dormancy.

The term "weed" refers to any plant which grows where not wanted.

The term "broadleaf" plant refers to any plant with a flat leaf. In weed control, it refers to nongrassy types of herbaceous plants.

The term "herbicide" refers to compounds or other substances intended for killing plants or interrupting their normal growth. It may be a broadleaf, grass or brush killer. Herbicides are used in five general ways: (1) preplanting: applied to after the soil has been prepared but before seeding; (2) pre-emergence (contact): non-residual dosages are used after seeding but before emergence of the crop seedlings; (3) pre-emergence (residual): applied at time of seeding or just prior to crop emergence, it kills weed seeds and germinating seedlings; (4) post-emergence: application after emergence of a crop; and (5) sterilant (non-selective): used to effect a complete kill of all treated plant life.

The term "selectivity" or "selective" refers to that characteristic in herbicides whereby certain undesirable species (or weeds) are killed while others such as crop plants are harmed little, or not at all.

DETAILED DESCRIPTION OF THE INVENTION

The compounds of the present invention may be prepared according to the following reaction sequence:

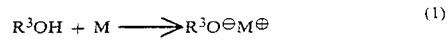
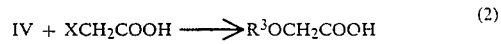
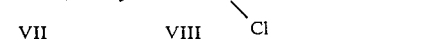

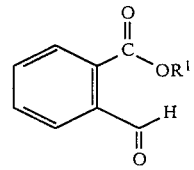

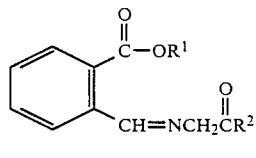

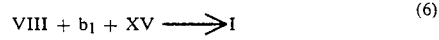

wherein $R^1$, $R^2$ and $R^3$ are as defined in conjunction with formula I, M is a Group Ia alkali metal or other strong base capable of abstracting a proton form a hydroxyl group, X is halogen and $b_1$ and $b_2$ are bases.

Reaction (1) is conducted by combing II and III. It is preferred to conduct the reaction under nitrogen. It is preferred to use an excess of II relative to III, on the order of from about 1.1 to about 20 equivalents II per equivalent III. Reactant II may be used as the solvent for Reaction (1), in such case a large excess of II is employed. Other suitable solvents include benzene, toluene, diethylether and the like. The reaction is carried out at a temperature of from about 0° C. to about 100° C., or for convenience at ambient temperature. The reaction is generally complete within about 1.0 to about 24 hours. The product, IV, conveniently used in Reaction (2) without further isolation and/or purification or alternatively may be isolated by conventional procedures such as removal of the solvent in vacuo, and the like.

Reaction (2) is conducted by combining at least two equivalents of IV and V in solvent. Preferably V in solvent is added to the prepared in situ IV. The reaction is conducted at a temperature of from about 0° C. to about 100° C., preferably from about 20° C. to about 80° C., or at reflux. The reaction is generally complete within about 2 to about 24 hours. Suitable solvents include low molecular weight alcohols such as isopropanol, ethanol, methanol, and the like; diethylether; tetrahydrofuran; 1,2-dimethoxyethane; and the like. If an alcohol is used as the solvent, it must be the same alcohol as reactant II otherwise there is a possibility of side reactions. The product VI is isolated by conventional procedures such as concentration in vacuo, washing, extraction, precipitation, distillation, and the like.

Reaction (3) is a conventional preparation of an acid chloride VIII from the corresponding carboxylic acid VI. For convenience, thionyl chloride, VII, is used. Other suitable reagents include oxalyl chloride, phosphorus trichloride, phosphorus pentachloride, and the like. The reaction is conducted by combining VI and VII in solvent. Although approximately equimolar amounts of VI and VII may be used, it is preferred to use an excess of VII relative to VI for more complete conversion to VIII, on the order of from about 1.1 to about 2.0 equivalents VII per equivalent VI. The reaction is conducted at a temperature of from about 0° C. to about 150° C., preferably from about 50° C. to about 120° C., or at reflux. The reaction is generally complete within about 2 to about 24 hours. Suitable solvents include inert organic solvents such as chloroform, dichloromethane, toluene, and the like. The product VIII is isolated by conventional procedures such as stripping concentration in vacuo, distillation, and the like, or, alternatively, after removal of excess thionyl chloride, VIII is used in Reaction (6) without further isolation.

Reaction (4) is conducted by combining IX, X and XI in solvent. It is preferred to slowly add XI to a stirred mixture of IX and X in solvent. It is preferred to use an excess of X and XI relative to IX, on the order of about 1 to about 3 moles X per mole IX and from about 1 to about 3 moles XI per mole IX. Suitable bases, $b_1$, include organic bases such as triethylamine, pyridine, and the like. The reaction is conducted at a temperature of from about 25° C. to about 150° C., preferably from about 30° C. to about 50° C., or at reflux, and is generally complete within about 2 to about 24 hours. Suitable solvents include inert organic solvents such as methylene chloride, benzene, chloroform, toluene, and the like. The product XII is isolated by conventional procedures such as extraction, washing, drying, vacuum distillation, concentration in vacuo, and the like.

Alternatively, XII may be prepared according to Reaction (4a). Reaction (4a) is conducted by combining IX, Xa and XIa in solvent. It is preferred to add an excess of Xa and XIa relative to IX, on the order to about 1.1 to about 4 moles Xa per mole IX and from about 1.1 to about 4 moles XIa per mole IX. Suitable bases, $b_2$, include inorganic bases such as potassium carbonate, sodium carbonate, sodium hydroxide, potassium hydroxide, and the like. The reaction is conducted at a temperature of from about 25° C. to about 150° C., preferably from about 50° C. to about 80° C. or at reflux, and is generally complete within about 3 to about 48 hours. Suitable solvents include polar, aprotic organic solvents such as acetone, dimethyl sulfoxide, acetonitrile, N,N-dimethylformamide, 1,2-dimethoxyethane, and the like. The product XII is isolated by conventional procedures such as extraction, washing, drying, vacuum distillation, concentration in vacuo, and the like.

Reaction (5) is conducted by combining XII, XIII and XIV in solvent. It is preferred to add XIII to XII and XIV in solvent. Although approximately equimolar amounts of XII and XIII may be used, it is preferred to use a slight excess of XIII. It is also preferred to add anhydrous magnesium sulfate XIV, in the range of approximately 2 moles to 4 moles XIV per mole XII, to the reaction mixture to remove water formed during the reaction. Alternatively, rather than using magnesium sulfate, the water formed during the reaction may be removed using other reagents or physical means well known to those skilled in the art. The amino acid derivative XIII is normally prepared just prior to use, since it may tend to dimerize upon standing. Reagent XIII is normally prepared from a salt, such as the hydrochloride or tosylate by conventional chemical methods. For example, the free form XIII may be conveniently generated by treatment with a base XI such as sodium hydroxide, potassium hydroxide, or triethylamine. It is preferred that an excess of base be used, on the order of from about 1 to about 3 equivalents base per equivalent XIII. The free form XIII also may be conveniently generated in situ. Reaction (5) is conducted at a temperature of from about 0° C. to about 50° C., preferably from about 0° C. to about 30° C. and is generally complete within about 1 to about 6 hours. Suitable solvents include inert organic solvents such as toluene, methylene chloride, benzene, chloroform, diethylether, and the like. The product XV is isolated by conventional procedures such as filtration, concentration in vacuo, and the like, or, alternatively, XV may be used in Reaction (6) after filtration to remove XIV, without further isolation.

Reaction (6) is conducted by combining VIII, XI and XV in solvent. Although approximately equimolar amounts of VIII, XI and XV may be used, it is preferred to use a slight excess of VIII and XI in relation to XV, on the order of about 1 to about 2 moles VIII per mole XV and from about 1 to about 2 moles XI per mole XV. The reaction is conducted at a temperature of about 0° C. to about 150° C., preferably from about 40° C. to about 80° C. and is generally complete within about 2 to about 8 hours. Suitable solvents include inert organic solvents such as toluene, methylene chloride, benzene, chloroform, diethylether, n-hexane, and the like. The product I is isolated by conventional procedures such as extraction, washing, concentration in vacuo, trituration, chromatography, recrystallization, and the like. Reaction (6) may produce a mixture of cis and trans isomers. The geometric isomers may be separated by conventional separation methods such as chromatography.

Reaction (6) may produce a mixture of geometric isomers. The conditions under which the reaction is conducted may influence which geometric isomer(s) is (or are) produced, and, if a mixture is produced, the relative ratio of trans:cis. It is believed that factors such as the solvent used, the temperatures at which the addition of the reactants and the reaction itself are conducted, and the order in which the reactants are combined may effect which isomer or isomers are formed. Thus, where n-hexane is the solvent used, a cis:trans isomer mixture is generally produced, whereas when the solvent is methylene chloride, benzene or toluene, formation of the trans isomer is favored. Conducting the reaction at a high temperature (e.g., at reflux), especially about 80° C., after the reactants have been combined generally favors formation of the trans isomer. Adding XV to IX in solvent followed by addition of XI favors formation of the trans isomer. Thus, if VIII is added to XV in solvent at about 0° C., followed by addition of XI and then the reaction mixture is heated to reflux, predominately trans isomer is formed.

Utility

The compounds of the present invention are surprisingly active as plant growth regulators, and may effect plant growth in a variety of ways.

The plant growth regulating effects (PGR) of the present invention include herbistatic activity and thus, they may retard growth in plants such as grasses (requiring less frequent mowing), bedding plants and trees. The compounds may also be used as chemical pruning agents for plants such as fruit trees and bushy ornamentals. Some of these compounds are useful in increasing yields in commercially important crops such as soybeans, and other broadleaf oil and seed crops. The compounds may be used as preconditioning agents for defoliation by promoting abscission and as agents for preventing late growth in crops such as cotton. Other PGR effects include increasing flowering and also affecting sex expression in flowering, for example, increasing the number of female flowers and thus the number of fruits produced in plants such as cucumbers. Other PGR effects are evidenced in the biological testing data in Tables II, XII and XIII.

The compounds of the present invention are, in general, herbicidal and plant-growth regulating in post emergent applications. As noted above, the compounds are particularly effective as post-emergent plant growth regulators.

The compounds, when applied to the soil surrounding growing plants in such an amount that the compounds will not kill beneficial plants, show efficient plant growth regulating or retarding effects.

The compounds of the present invention also exhibit plant growth regulating activity and especially root growth inhibition; foliage regrowth inhibition and crop enhancement. The former activity is useful where top growth is desirable. Foliage regrowth inhibition is desirable in cases such as the harvesting of cotton. In harvesting cotton, defoliants and desiccants are frequently used to remove the leaves of the cotton plant thus making the cotton more accessible. In such cases regrowth inhibitors are useful to inhibit the regrowth of leaves, before harvesting is completed. Crop and flower enhancements are produced by pinching and increasing crop- and flower-bearing branching in crops such as soybeans and chrysanthemums. These compounds exhibit activity in potato sprout inhibition; they reduce both the number and growth (length) of sprouts from the eyes of potato tubers.

The present compounds of Formula I can be applied in pure form, but more pragmatically, are applied in combination with a carrier. The same types of carriers as set forth hereinabove with respect to the herbicide compositions can also be used. Depending on the desired application, the plant growth regulating composition can also contain, or be applied in combination with other compatible ingredients such as desiccants, defoliants, surface-active agents, adjuvants, fungicides, insecticides and selective herbicides. Typically, the plant growth regulating composition will contain a total of about from 0.005 to 90 wt. %, of the compound(s) of Formula I depending on whether the composition is intended to be applied directly or diluted first.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert a growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as china clays, diatomaceous earth, synthetic fine silica, calcium silicate and other inert solid carriers of the kind conventionally employed in powdered growth-regulating compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

The amount of compound or composition administered will vary with the particular plant part or plant growth medium which is to be contacted, the general location of application—i.e., sheltered areas such as greenhouses, as compared to exposed areas such as fields—as well as the desired type of control. For plant growth regulating or retarding activity, it is essential to apply the compounds at a concentration not so high as to kill the plants. Therefore, the application rates for plant growth regulating or retarding activity will generally vary from 0.1 to 5 kg/ha, and preferably from 0.1 to 3 kg/ha.

The compounds of Formula IA exhibit very good pre-emergence herbicidal activity against both grasses and broadleaf plants. These compounds also exhibit very good post-emergence herbicidal activity against both grasses and broadleaf plants. Further, by proper reduction of the dosage, the compounds can be safely applied as selective post-emergence herbicides to reduce or prevent the growth of broadleaf weeds and some grasses amongst (broadleaf) crops, such as soybeans.

Generally, for post-emergent applications the herbicidal compounds are applied directly to the foliage or other plant parts. For pre-emergence applications, the herbicidal compounds are applied to the growing medium, or prospective growing medium, of the plant. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having higher concentrations designed for dilution prior to application. The carrier can be a solid, liquid, or aerosol. The actual compositions can take the form of granules, powders, dusts, solutions emulisions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for preemergence application agents which reduce the leachability of the compound.

The composition can also contain various compatible adjuvants, stabilizers, conditioners, insecticides, fungicides, and if desired, other herbicidally active compounds.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Also where necessary examples are repeated to provide additional starting material for subsequent examples.

A further understanding of my invention may be found in the following non-limiting examples.

EXAMPLES

EXAMPLE 1

Preparation of

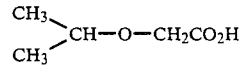

(1-Methylethoxy)acetic acid

To a 3-neck 2-liter round-bottom flask equipped with a mechanical stirrer, reflux condenser and addition funnel was added 1000 ml of 2-propanol under nitrogen. Sodium spheres (34.75 g, 1.511 moles) were then added and the mixture stirred without heating for 2 hours. The mixture was then heated at reflux for 2 hours to completely dissolve the remaining sodium. After cooling the mixture to room temperature, a solution of bromoacetic acid (100.00 g, 0.720 moles) in 200 ml of 2-propanol was added dropwise and the mixture then heated again at reflux for 3 hours. After stirring overnight at room temperature, the mixture was concentrated in vacuo to remove the 2-propanol and the resulting white solid dissolved in 200 ml of water. This aqueous solution was washed with ether (3×75 ml) and then acidified to pH 1 with concentrated hydrochloric acid. The resulting mixture was extracted with ether (3×100 ml) and the combined extracts washed with saturated sodium chloride solution (1×75 ml), dried over magnesium sulfate and concentrated in vacuo to give 41.0 g of the product as a colorless oil.

EXAMPLE 2

Preparation of

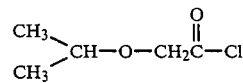

(1-Methylethoxy)acetyl chloride

To a 3-neck 500 ml round-bottom flask equipped with a magnetic stirrer, reflux condenser and addition funnel was added (1-methylethoxy)acetic acid (40.00 g, 0.339 moles) and 200 ml of chloroform under nitrogen. Thionyl chloride (80.57 g, 0.677 moles) was then added dropwise. After the addition was complete, the solution was refluxed for 6 hours and then stirred at room temperature overnight. The mixture was then concentrated in vacuo to give 34.1 g of the product as a yellow oil.

EXAMPLE 3

Preparation of

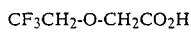
CF$_3$CH$_2$-O-CH$_2$CO$_2$H (2,2,2-Trifluoroethoxy)acetic acid

To a 3-neck 2-liter round-bottom flask equipped with a mechanical stirrer, reflux condenser and addition funnel was added sodium hydride (60% dispersion in mineral oil) (41.70 g, 1.043 moles) and 1000 ml of toluene under nitrogen. 2,2,2-Trifluoroethanol (52.02 g, 0.520 moles) was added dropwise and this mixture was stirred at room temperature for 0.5 hours. A solution of bromoacetic acid (72.45 g, 0.520 moles) in 100 ml of toluene was then added dropwise and the resulting mixture heated at reflux for 48 hours. After cooling the mixture to room temperature, water (250 ml) was added and the layers separated. The aqueous layer was washed with ether (3×75 ml) and then acidified to pH 1 with concentrated hydrochloric acid. The resulting mixture was extracted with ether (3×100 ml) and the combined extracts washed with saturated sodium chloride solution (1×75 ml), dried over magnesium sulfate and concentrated in vacuo to give a yellow oil. Distillation of this oil gave 31.6 g of the product as a colorless oil, bp 110°–118° C./16 mm.

EXAMPLE 4

Preparation of

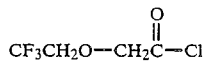

(2,2,2-Trifluoroethoxy)acetyl chloride

To a 3-neck 500 ml round-bottom flask equipped with a magnetic stirrer, reflux condenser and addition funnel was added (2,2,2-trifluoroethoxy)acetic acid (30.90 g, 0.196 moles) and 250 ml of chloroform under nitrogen. Thionyl chloride (30.20 g, 0.250 moles) was added dropwise and the solution refluxed for 2 hours. The mixture was then concentrated by distillation of the chloroform and excess thionyl chloride. The remaining yellow oil was distilled in vacuo to give 18.9 g of the product as a colorless oil, bp 40°–48° C./20 mm.

EXAMPLE 5

Preparation of

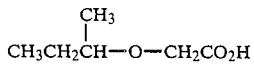

(1-Methylpropoxy)acetic acid

To a 3-neck 1-liter round-bottom flask equipped with a mechanical stirrer, reflux condenser and addition funnel was added 500 ml of 2-butanol under nitrogen. Sodium spheres (3.31 g, 0.144 moles) were then added and the mixture heated at reflux for 6 hours and then stirred at room temperature overnight. A solution of bromoacetic acid (10.00 g, 0.072 moles) in 10 ml of 2-butanol was then added dropwise and the mixture stirred at room temperature for 24 hours. The mixture was then concentrated in vacuo to remove the 2-butanol and the resulting white solid dissolved in 100 ml of water. This aqueous solution was washed with ether (2×50 ml) and then acidified to pH 1 with concentrated hydrochloric acid. The resulting mixture was extracted with ether (3×100 ml) and the combined extracts washed with saturated sodium chloride solution (1×50 ml), dried over magnesium sulfate and concentrated in vacuo to give 8.1 g of the product as a pale yellow oil.

EXAMPLE 6

Preparation of

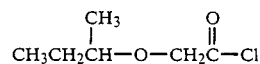

(1-Methylprgpoxy)acetyl chloride

To a 3-neck 250 ml round-bottom flask equipped with a magnetic stirrer, reflux condenser and addition funnel was added (1-methylpropoxy)acetic acid (8.10 g, 0.060 moles) and 100 ml of chloroform under nitrogen. Thionyl chloride (9.50 g, 0.080 moles) was added dropwise and the solution then heated at reflux for 2 hours. The mixture was then concentrated by distillation of the chloroform and excess thionyl chloride. The remaining yellow oil was distilled in vacuo to give 6.0 g of the product as a colorless oil, bp 54°–63° C./16 mm.

EXAMPLE 7

Preparation of

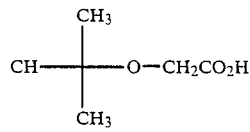

(1,1-Dimethylethoxy)acetic acid

To a 3-neck 2-liter round-bottom flask equipped with a mechanical stirrer, reflux condenser and addition funnel was added potassium tert-butoxide (100.00 g, 0.891 moles) and 1500 ml of toluene under nitrogen. A solution of bromoacetic acid (61.90 g, 0.446 moles) in 100 ml of toluene was then added dropwise and the mixture then heated at reflux for 24 hours. After cooling the mixture to room temperature, water (100 ml) was added and the layers separated. The aqueous layer was washed with ether (2×50 ml) and then acidified to pH 1 with concentrated hydrochloric acid. The resulting mixture was extracted with ether (3×100 ml) and the combined extracts washed with saturated sodium chloride solution (1×75 ml), dried over magnesium sulfate and concentrated in vacuo to give 27.3 g of the product as a yellow oil.

EXAMPLE 8

Preparation of

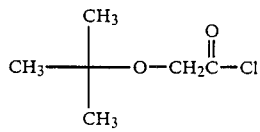

(1,1-Dimethylethoxy)acetyl chloride

To a 3-neck 500 ml round-bottom flask equipped with a magnetic stirrer, reflux condenser and addition funnel was added (1,1-dimethylethoxy)acetic acid (24.00 g, 0.182 moles) and 300 ml of toluene under nitrogen. Oxalyl chloride (46.10 g, 0.363 moles) was then added dropwise and to this mixture was added N,N-dimethylformamide (0.25 g, 0.003 moles). This solution was heated at 30°–40° C. for 5 hours and then concentrated in vacuo to give 14.5 g of the product as a brown oil.

EXAMPLE 9

Preparation of

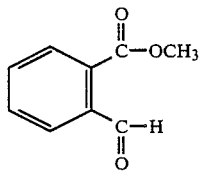

2-Carbomethoxybenzaldehyde

To a 3-neck 1-liter round-bottom flask equipped with a magnetic stirrer, reflux condenser and addition funnel was added 2-carboxybenzaldehyde (100.00 g, 0.659 moles), dimethylsulfate (162.8 g 1.291 moles) and 200 ml of dichloromethane under nitrogen. The mixture was heated to reflux and triethylamine (135.89 g, 1.343 moles) was added at such a rate to maintain a brisk reflux. After the addition was complete, the solution was allowed to cool to room temperature and stirred overnight. Water (400 ml) was then added and the layers separated. The aqueous layer was extracted with dichloromethane (1×200 ml) and the combined organic layers washed with saturated sodium bicarbonate solution (1×400 ml), dried over magnesium sulfate and concentrated in vacuo to give a golden oil. Vacuum distillation of this oil gave 88.7 g of the product as a pale yellow oil, bp 95°–98° C./0.4 mm.

EXAMPLE 10

Preparation of

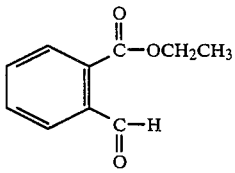

2-Carboethoxybenzaldehyde

To a 3-neck 500 ml round-bottom flask equipped with a magnetic stirrer, reflux condenser and addition funnel was added 2-carboxybenzaldehyde (30.00 g, 0.200 moles), diethylsulfate (33.92 g, 0.220 moles) and 150 ml of dichloromethane under nitrogen. The mixture was heated to reflux and triethylamine (30.36 g, 0.300 moles) was added at such a rate to maintain a brisk reflux. After the addition was complete, the solution was heated at reflux for 1 hour and then allowed to cool to room temperature and stirred overnight. The mixture was then washed with water (1×50 ml), 1.0N hydrochloric and solution (1×50 ml), saturated sodium bicarbonate solution (1×50 ml), saturated sodium chloride solution (1×50 ml), dried over magnesium sulfate and concentrated in vacuo to give 21.0 g of the product as a pale yellow oil.

EXAMPLE 11

Preparation of

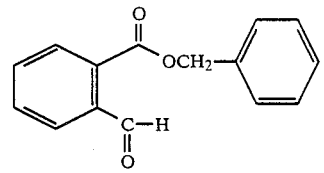

2-Carbobenzoxybenzaldehyde

A mixture of 2-carboxybenzaldehyde (15.00 g, 0.100 moles), benzyl bromide (20.52 g, 0.120 moles) and potassium carbonate (41.46 g, 0.300 moles) in 250 ml of acetone under nitrogen in a 500 ml round-bottom flask equipped with a magnetic stirrer was refluxed for 6 hours and then stirred at room temperature overnight. The mixture was then filtered through Celite and the filtrate concentrated in vacuo to remove the acetone. The remaining yellow oil was dissolved in ether (200 ml) and this solution washed with saturated sodium bicarbonate solution (1×50 ml), saturated sodium chloride solution, dried over magnesium sulfate and concentrated in vacuo to give 20.4 g of the product as a yellow oil.

EXAMPLE 12

Preparation of

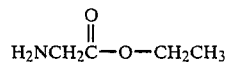

Glycine Ethyl Ester

To a 250 ml round-bottom flask under nitrogen equipped with a magnetic stirrer was added a 50% aqueous solution of sodium hydroxide (6.40 g, 0.080 moles) and 100 ml of dichloromethane. This mixture was cooled to 0° C. and glycine ethyl ester hydrochloride was added in one portion. The mixture was stirred at 0° C. for 10 minutes and then the dichloromethane layer was decanted from the aqueous layer. The dichloromethane layer was dried over magnesium sulfate and the concentrated in vacuo to give 5.40 g of the product as a pale yellow oil. This oil was used immediately in subsequent reactions, since it dimerizes to 2,5-piperazinedione on standing at room temperature.

EXAMPLE 13

Preparation of

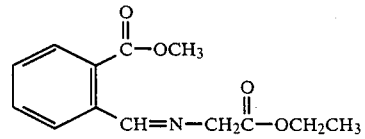

Ethyl (N-2-carbomethoxybenzylidenyl)glycine

To a 250 ml round-bottom flask equipped with a magnetic stirrer was added 2-carbomethoxybenzaldehyde (8.00 g, 0.049 moles), anhydrous magnesium sulfate (24.10 g, 0.200 moles) and 100 ml of toluene under nitrogen. Glycine ethyl ester (5.00 g, 0.049 moles) was then added and this mixture stirred at room temperature for 1 hour. The magnesium sulfate was then removed by filtration through Celite to give a pale yellow solution of the product in toluene. This solution was used in subsequent reactions without further purification.

EXAMPLE 14

Preparation of

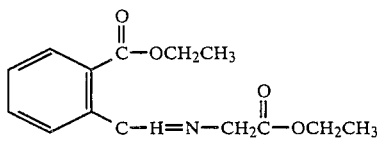

Ethyl (N-2-carboethoxybenzylidenyl)glycine

To a 250 ml round-bottom flask equipped with a magnetic stirrer was added 2-carboethoxybenzaldehyde (2.90 g, 0.016 moles), anhydrous magnesium sulfate (6.50 g, 0.050 moles) and 75 ml of toluene under nitrogen. Glycine ethyl ester (1.70 g, 0.016 moles) was then added and this mixture stirred at room temperature for 1 hour. The magnesium sulfate was then removed by filtration through Celite to give a pale yellow solution of the product in toluene. This solution was used in subsequent reactions without further purification.

EXAMPLE 15

Preparation of

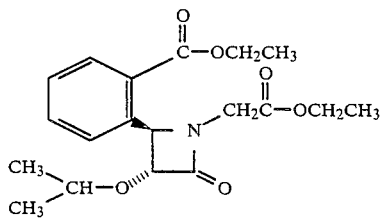

trans-1-Carboethoxymethyl-3-(1-methylethoxy)-4-(2'-carboethoxyphenyl)acet-2-one

To a 3-neck 250 ml round-bottom flask equipped with a magnetic stirrer, reflux condenser, addition funnel and a thermometer was added a solution of ethyl (N-2-carboethoxybenzylidenyl)glycine (4.06 g, 0.016 moles) in approximately 75 ml of toluene under nitrogen. This solution was cooled to 0° C. and (1-methylethoxy)acetyl chloride (3.30 g, 0.24 moles) added dropwise. The resulting solution was stirred at 0° C. for 1 hour and then triethylamine (2.00 g, 0.019 moles) was added dropwise. After the addition was complete, the solution was heated at 70° C. for 2 hours and then stirred at room temperature overnight. The mixture was then washed with water (1×25 ml), 1.0N hydrohloric acid (1×25 ml), 1.0N sodium hydroxide solution (1×25 ml), saturated sodium chloride solution (1×25 ml), dried over magnesium sulfate and concentrated in vacuo to give 3.5 g of a yellow oil.

This oil was purified by preparative liquid chromatography performed on a Waters PrepLC/System 500 using a PrepPAK 500 silica gel column and 33% ethyl acetate/hexane as eluent. The fraction with an approximate $R_f$ of 0.2 was collected and concentrated in vacuo to give 1.1 g of the product as a yellow oil.

EXAMPLE 16

Preparation of

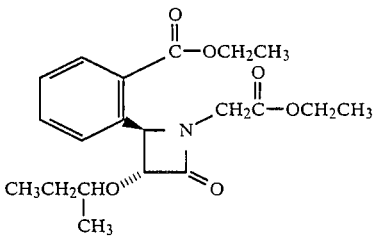

trans-1-Carboethoxymethyl-3-(1-methylpropoxy)-4-(2'-carbomethoxyphenyl)azet-2-one To a 3-neck 500 ml round-bottom flask equipped with a magnetic stirrer, reflux condenser, addition funnel and a thermometer was added a solution of ethyl (N-2-carbomethoxybenzylidenyl)glycine (6.61 g, 0.027 moles) in approximately 100 ml of toluene under nitrogen. This solution was cooled to 0° C. and (1-methylpropoxy)acetyl chloride (6.00 g, 0.040 moles) was added dropwise. The resulting solution was stirred at 0° C. for 1 hour and then triethylamine (3.20 g, 0.032 moles) was added dropwise. The resulting solution was heated at 70° C. for 2 hours and then stirred at room temperature overnight. The mixture was then washed with water (1×50 ml), 1.0N hydrochloric acid (1×50 ml), 1.0N sodium hydroxide solution (1×50 ml), saturated sodium chloride solution (1×50 ml), dried over magnesium sulfate and concentrated in vacuo to give 4.7 g of an orange oil.

This oil was purified by preparative liquid chromatography performed on a Waters PrepLC/System 500 using a PrepPAK 500 silica gel column and 33% ethyl acetate/hexane as eluent. The fraction with an approximate $R_f$ of 0.22 was collected and concentrated in vacuo to give 3.0 g of the product as an orange oil.

Elemental analysis for $C_{19}H_{25}NO_6$ showed: calculated % C 62.8, % H 6.9, % N 3.85; found % C 61.6, H 8.1, % N 3.7.

EXAMPLE 17

Preparation of

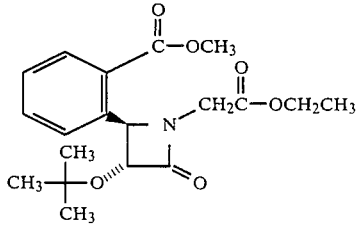

trans-1-Carboethoxymethyl-3-(1,1-dimethylethoxy)-4-(2'-carbomethoxyphenyl)azet-2-one To a 3-neck 500 ml round-bottom flask equipped with a magnetic stirrer, reflux condenser, addition funnel and a thermometer was added a solution of ethyl (N-2-carbomethoxybenzylidenyl)glycine (15.95 g, 0.064 moles) in approximately 150 ml of toluene under nitrogen. This solution was cooled to 0° C. and (1,1-dimethylethoxy)acetyl chloride (14.50 g, 0.096 moles) was added dropwise. The resulting solution was stirred at 0° C. for 1 hour and then triethylamine (7.80 g, 0.077 moles) was added dropwise. The resulting solution was heated at 70° C. for 2 hours and then stirred at room temperature overnight. The mixture was then washed with water (1×50 ml), 1.0N hydrochloric acid (1×50 ml), 1.0N sodium hydroxide solution (1×50 ml), saturated sodium chloride solution (1×50 ml), dried over magnesium sulfate and concentrated in vacuo to give 15.4 g of a brown oil.

This oil was purified by preparative liquid chromatography performed on a Waters PrepLC/System 500 using a PrepPAK 500 silica gel column and 50% ethyl acetate/hexane as eluent. The fraction with an approximate $R_f$ of 0.45 was collected and concentrated in vacuo to give a yellow oil. This oil was further purified by chromatography as above using 40% ethyl acetate/hexane as eluent. The fraction with an approximate $R_f$ of 0.4 was collected and concentrated in vacuo to give 3.0 g of the product as a yellow oil.

Elemental analysis for $C_{19}H_{25}NO_6$ showed: calculated % C 62.8, % H 6.9, % N 3.85; found % C 62.6, H 7.4, % N 6.45.

EXAMPLE 18

Preparation of trans-1-Carboethyoxymethyl-3-(2,2,2-trifluoroethoxy)-4-(2'-carbomethoxyphenyl)azet-2-one To a 3-neck 500 ml round-bottom flask equipped with a magnetic stirrer, reflux condenser, addition funnel and a thermometer was added a solution of ethyl (N-2-carbomethoxybenzylidenyl)glycine (17.44 g, 0.070 moles) in approximately 200 ml of toluene under nitrogen. This solution was cooled to 0° C. and (2,2,2-trifluoroethoxy)acetyl chloride (18.90 g, 0.105 moles) was added dropwise. The resulting solution was stirred at 0° C. for 1 hour and then triethylamine (8.50 g, 0.080 moles) was added dropwise. After the addition was complete, the solution was heated at 70° C. for 2 hours and then stirred at room temperature overnight. The mixture was then washed with water (1×75 ml), 1.0N hydrochloric acid (1×75 ml), 1.0N sodium hydroxide solution (1×50 ml), saturated sodium chloride solution (1×75 ml), dried over magnesium sufate and concentrated in vacuo to give 20.1 g of a yellow oil.

A 10.0 g sample of this oil was purified by preparative liquid chromatography performed on a Waters PrepLC/System 500 using a PrepPAK 500 silica gel column and 33% ethyl acetate/hexane as eluent. The fraction with an approximate $R_f$ of 0.3 was collected and concentrated in vacuo to give 3.3 g of the product as a yellow oil.

Compounds made in accordance with the methods described in the Detailed Description of the Invention and in Examples 1 to 18 and using the appropriate starting materials are found in Table I.

In addition, by following the methods outlined in the Detailed Description of the Invention and disclosed in Examples 1 to 18 and using the appropriate starting materials and reagents, the following compounds are made:

trans-1-carboethoxymethyl-3-(trifluoromethoxy)-4-(2'-carbomethoxyphenyl)azet-2-one;
trans-1-carboethoxymethyl-3-(pentafluoroethoxy)-4(2'-carbomethoxyphenyl)azet-2-one;
trans-1-carboethoxymethyl-3-(1-methyl-2,2,2-trifluoroethoxy)-4-(2'-carbomethoxyphenyl)azet-2-one;
trans-1-carboethoxymethyl-3-(1,1-dimethyl-2,2,2-trifluoroethoxy)-4-(2'-carbomethoxyphenyl)azet-2-one;
trans-1-carboethoxymethyl-3-(chloromethoxy)-4-(2'-carbomethoxyphenyl)azet-2-one;
trans-1-carboethoxymethyl-3-(2-chloroethoxy)-4-(2'-carbomethoxyphenyl)azet-2-one;
trans-1-carboethoxymethyl-3-(2,2,2-trichloroethoxy)4-(2'-carbomethoxyphenyl)azet-2-one;
trans-1-carboethoxymethyl-3-(cyclopropoxy)-4-(2'-carbomethoxyphenyl)azet-2-one;
trans-1-carboethoxymethyl-3-(cyclopropylmethoxy)-4(2'-carbomethoxyphenyl)azet-2-one;
trans-1-carboethoxymethyl-3-(cyclobutoxy)-4-(2'-carbomethoxyphenyl)azet-2-one;
trans-1-carboethoxymethyl-3-(1,2-dimethylpropoxy)-4(2'-carbomethoxyphenyl)azet-2-one;
trans-1-carboethoxymethyl-3-(ethylenoxy)-4-(2'-carbomethoxyphenyl)azet-2-one;
trans-1-carboethoxymethyl-3-(3-chloro-2-propenoxy)-4(2'-carbomethoxyphenyl)azet-2-one;
trans-1-carboethoxymethyl-3-(methoxymethoxy)-4-(2'-carbomethoxyphenyl)azet-2-one;
trans-1-carboethoxymethyl-3-(methylthiomethylene)-4(2'-carbomethoxyphenyl)azet-2-one; trans-1-carboethoxymethyl-3-(ethylthiomethylene)-4(2'-carbomethoxyphenyl)azet-2-one; trans-1-carbomethoxymethyl-3-(1-methylethoxy)-4-(2'-carboethoxyphenyl)azet-2-one; trans-1-carbopropoxymethyl-3-(1-methylethoxy)-4-(2'-carboethoxyphenyl)azet-2-one; trans-1-carbo(1-methylethoxy)methyl-3-(1-methylethoxy)-4-(2'-carboethoxyphenyl)azet-2-one; trans-1-carbobutoxymethyl-3-(1-methylethoxy)-4-(2'-carboethoxyphenyl)azet-2-one; trans-1-carbo(1-methylpropoxy)methyl-3-(1-methylethoxy)-4-(2'-carboethoxyphenyl)azet-2-one; trans-1-carbo(2-methylpropoxy)methyl-3-(1-methylethoxy)-4-(2'-carboethoxyphenyl)azet-2-one; trans-1-carbo(phenylmethoxy)methyl-3-(1-methylethoxy)-4-(2'-carboethoxyphenyl)azet-2-one; trans-1-carboethoxymethyl-3-(1,1-dimethylethoxy)-4(2'-carboethoxyphenyl)azet-2-one; trans-1-carboethoxymethyl-3-(2,2,2-trifluoroethoxy)-4-(2'-carboethoxyphenyl)azet-2-one; trans-1-carboethoxymethyl-3-(1-methyl-2,2,2-trifluoroethoxy)-4-(2'-carboethoxyphenyl)azet-2-one; trans-1-carboethoxymethyl-3-(1,1-dimethyl-2,2,2-trifluoroethoxy)-4-(2'-carboethoxyphenyl)azet-2-one; trans-1-carboethoxymethyl-3-(1,1-dimethylethoxy)-4(2'-carboethoxyphenyl)azet-2-one; trans-1-carboethoxymethyl-3-(2,2,2-trifluoroethoxy)-(2'-carboethoxyphenyl)azet-2-one; trans-1-carboethoxymethyl-3-(1-methyl-2,2,2-trifluoroethoxy)-4-(2'-carboethoxyphenyl)azet-2-one; trans-1-carboethoxymethyl-3-(1,1-dimethyl-2,2,2-trifluoroethoxy)-4-(2'-carboethoxyphenyl)azet-2-one; trans-1-carboethoxymethyl-3-(1,1-dimethlethoxy)-4(2'-carboethoxyphenyl)azet-2-one; trans-1-carboethoxymethyl-3-(2,2,2-trifluoroethoxy)-(2'-carboethoxyphenyl)azet-2-one; trans-1-carboethoxymethyl-3-(1-methyl-2,2,2-trifluoroethoxy)-4-(2'-carboethoxyphenyl)azet-2-one; and
trans-1-carboethoxymethyl-3-(1,1-dimethyl-2,2,2-trifluoroethoxy)-4-(2'-carboethoxyphenyl)azet-2-one.

EXAMPLE A

Axillary Bud Inhibition Foliar Spray

The compounds of this invention were tested to determine their effect on axillary bud growth of Pinto Beans.

Pinto Bean plants, one pot per test compound (one plant per pot) were sprayed with an acetone-water carrier solution which contained a small amount of nonionic emulsifier with a concentration of 200 ppm (or 625 ppm where noted) of test compound. A pot sprayed with the carrier solution without test compound was used as a check. One pot was sprayed with 100 ppm 1-naphthyleneacetic acid as a standard. After spraying the solution was allowed to dry on the plant leaves; the plants were then transferred to a greenhouse maintained at 70-80° F. and the plants were randomized.

The plants were read 12 days after treatment. Bud growth at the axil of the monofoliate leaf was read and expressed as % inhibition of axillary growth as compared to the untreated check topped above the monofoliate leaves. Results are given in Table II.

EXAMPLE B

Germination and Seedling Development Test

The compounds of this invention were tested to determine their effect on seed germination, seedling shoot and root development in two types of plant, mung beans and barnyard grass.

Seed pouches containing mung bean and barnyard grass seeds were treated with 15 ml of a solution containing 30 ppm (or 40 ppm where noted) of test compound in a water-acetone carrier formulation which contained a small amount of nonionic emulsifier. A seed pouch treated with carrier formulation without test compound was used as a check. The seed pouches were then held under about 125–150 foot-candles of light for 24 hours per day for 7 days at room temperature.

Root length was measured for each species and expressed as % root inhibition as compared to the check.
Results are given in Table II.

EXAMPLE C

Ethylene Evolution Test

The compounds of this invention were tested to determine their effect on ethylene evolution in plant tissue. Ethylene gas is a natural plant growth regulator which is produced by the plant when a change in growth or development occurs. Active levels of ethylene production from the leaf disc explant system may indicate wounding or damage to the plant tissue, a change in the enzyme or hormonal balance within the leaf disc, the onset of senescence of the leaf, or an increase in the metabolic rate of the tissue.

Vials each with two leaf discs cut from the monofoliate leaf of the pinto bean were treated with one ml of a $10^{-5}$ 6-benzylaminopurine solution (BAP) and one ml of a 80 ppm (or 100 ppm or 250 ppm where noted) acetone-water solution of test compound which contained a small amount of nonionic emulsifier. After treatment, the vials were capped and the time of capping noted. The vials were then incubated for 18 hours at room temperature in diffuse light. Vials containing one ml of BAP and one ml of 2% aqueous acetone were used as checks.

After incubation, one ml of gas mixture is removed from the upper portion of the vial and tested with a gas chromatograph. The data is recorded as % of reference where reference is 5 ppm ethylene in nitrogen gas. Results are given in Table II.

EXAMPLE D

Cotton Defoliation, Desiccation and Regrowth Inhibition

The compounds of this invention were tested to determine their effect on defoliation, desiccation and regrowth of cotton.

Cotton plants 4 to 5 weeks old having 4 true leaves above the cotyledonary leaves from which growth beyond the second true leaf had been removed not longer than 24 hours before treatment were used as test plants. The plants are treated by spraying with a 2000 ppm solution of test compound in an acetone-water carrier formulation which contained a small amount of nonionic emulsifier. A plant sprayed with carrier formulation without test compound was used as the untreated check. An hour after spraying, the plants were transferred to a greenhouse maintained at about 85° F. (±5° F.) where they were allowed to incubate for 13 to 18 days before evaluation.

Defoliation or desiccation of each of the four leaves on each plant was evaluated, each leaf being 25% of the total. The combined defoliation/desiccation percentages cannot exceed 100%, since a leaf which both abscises and desiccates is noted only as "Defoliation".

Regrowth was noted as % inhibition of axillary bud growth as compared to the untreated check. Results are given in Table II.

EXAMPLES E and F

The compound was respectively tested for pre-emergent and post-emergent activity against a variety of grasses and broad-leaf plants including one grain crop and one broad-leaf crop.

EXAMPLE E

Pre-Emergent Herbicide Test

Pre-emergence herbicidal activity was determined in the following manner.

An acetone solution of the test compound was prepared by mixing 750 mg of the test compound, 220 mg of a nonionic surfactant and 25 ml of acetone. This solution was added to approximately 125 ml of water containing 156 mg of surfactant.

Seeds of the test vegetation were planted in a pot of soil and the test compound solution was sprayed uniformly onto the soil surface at a dose of 27.5 micrograms/cm². The pot was watered intermittently and was observed for seedling emergence, health of the emerging seedlings, etc., for a 3-week period. At the end of this period the herbicidal effectiveness of the test compound was rated based on the physiological observations. A 0-to-100-scale was used, 0 representing no phytotoxicity and 100 representing complete kill. The results of these tests are summarized in Table III, hereinbelow.

EXAMPLE F

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 27.5 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the copound was rated based on these observations. A 0-to-100-scale was used, 0 representing no phytotoxicity and 100 representing complete kill. The results of these tests are summarized in Table III.

EXAMPLE G

Post-Emergence Herbicidal Test

Post-emergence herbicidal activity (in the greenhouse) for comparison with known compounds was determined in the following manner:

A stock solution consisting of 56.7 mg of test compound, 17 ml acetone and 45 mg of Ortho X77 Spreader was prepared. 10, 4, 1.6 and 0.64 alignments of this stock solution were added to enough diluent to make 50 ml of spray formulations. When sprayed, this resulted in application rates of 4.4, 1.76, 0.7 and 0.28 microgram/cm$^2$. Diluent consisted of 0.625 g Ortho X-77 per liter of deionized water.

The stock solution for the rates of 1.8, 0.72, 0.29 and 0.12 consisted of 22.7 mg of test compound, 17 ml of water and 45 mg of Ortho X-77.

Where formulated compounds were used, deionized water replaced acetone in the stock solution and no Ortho X-77 was added.

The test formulation was uniformly sprayed on 2 similar pots containing plants 2 to 3 inches tall (except wild oats, soybean and watergrass which were 3 to 4 inches tall) (approximately 5 to 10 plants per species) at the test compound doses given in Tables II to V. After the plants had dried, they were placed in a greenhouse and were sub-irrigated. The plants were observed periodically for phytotoxic effects and physiological and morphological responses to the treatment. The herbicidal effectiveness of the compound was rated based on these observations and the test was scored at the time(s) after treatment as noted on the Tables. A 0-to-100 scale was used 0 representing no phytotoxicity, 100 representing complete kill. The results of these tests are summarized in Tables V to VIII.

EXAMPLE H

Pre-Emergence Herbicidal Test

Pre-emergence herbicidal activity for comparison with known compounds was determined in the following manner.

The test compounds were formulated in the same manner as described in Example G for the post-emergence tests.

Seeds of the test vegetation were planted in a pot of soil and the test solution was sprayed uniformly onto the soil surface at a test compound dose of 4.4 micrograms/cm$^2$ unless otherwise specified in Table IX. The pot was watered and placed in a greenhouse. The pot was watered intermittently and observed for seedling emergence, health of emerging seedlings, etc. The herbicidal effectiveness of the compound was rated based on the physiological observations at the time after treatment noted in Table VI. A 0-to-100 scale was used, 0 representing no phytotoxicity, 100 representing complete kill. The results of these tests are summarized in Table IX.

EXAMPLE I

Post-Emergence Herbicidal Test

Post-emergence herbicidal activity under field conditions was determined in the following manner:

The test formulation was uniformly sprayed on one replicate containing 31 to 156 plants depending on the species. Plants were 2-4-leaf stage at the time of treatment. Plot size was 5.5 × 1.5 meters. There was one row of each species/plot. The rates of 1.0, 0.5, 0.25, and 0.062 Kg/ha were applied in 250 liters of spray containing 1% v/v Assist adjuvant.

Twenty days after treatment, the plots were rated using the linear scale of 0 to 100, where 0 indicates no effect and 100 indicates complete kill (Table X). Twenty-five days after treatment, the height of soybeans, cotton and Morning Glory were measured in centimeters (Table XI).

EXAMPLE J

Potato Sprout Inhibition

Compounds were tested for their activity in inhibiting sprouting in potato tubers according to the following procedure.

A stock solution of test compound was prepared containing 300 mg compound, 150 mg Ortho X-77 Spreader and acetone. For compounds insoluble in water or acetone, a wet grind was used in preparing the stock solution. Stock solution was added to deionized water: 18 ml to 182 ml water, 6 ml to 194 ml water and 2 ml to 198 ml water to give test concentrations of 900 ppm, 300 ppm and 100 ppm, respectively. A check solution was made using 18 ml acetone, 90 mg Ortho X-77 Spreader and 192 ml deionized water.

Portions of potato tubers (each containing an eye) ("potato sections") were incubated for several days in a humid atmosphere at about 45°–50° C. until they became suberized.

Potato sections, twenty per concentraton of test compound and checks, were dipped in test formulation and then shaken lightly for one minute. Treated potato sections were placed in Petri dishes (5 per dish) containing moist, sterilized sand which were then incubated in a dark incubator at 70°–75° F.

The tests were evaluated at the time after treatment indicated (after the controls have developed a measurable amount of vegetative growth, usually 4 to 5 weeks after treatment. The number and length of sprouts were measured. Percent of check was calculated according to the following formula:

Percent of check = $\frac{\text{Length Treated Sprouts}}{\text{Length Check Sprouts}} \times 100$ Results are tabulated in Table XII.

TABLE I

Compounds of the Formula:

[Structure: a benzene ring with a C(=O)–OR¹ group ortho to a β-lactam ring bearing an N–CH₂–C(=O)–OCH₂CH₃ substituent and an OR³ group]

| Compound No. | | Configu-ration | R¹ | R³ | Physical State | ELEMENTAL ANALYSIS | | | | | |
|---|---|---|---|---|---|---|---|---|---|---|---|
| | | | | | | % C | | % H | | % N | |
| | | | | | | Calc. | Found | Calc. | Found | Calc. | Found |
| 1 | 46496 | trans | —CH₃ | —H | yellow oil | 58.6 | 51.95 | 5.6 | 5.38 | 4.55 | 5.15 |
| 2 | 46095 | trans | —CH₃ | —CH₃ | yellow solid, m.p. 47–49° C. | 59.8 | 60.6 | 5.95 | 6.0 | 4.35 | 3.75 |
| 3 | 46019 | trans | —CH₃ | —CH₂CH₃ | yellow oil | 60.9 | 57.7 | 6.3 | 7.1 | 4.2 | 4.25 |
| 4 | 46183 | cis | —CH₃ | —CH₂CH₃ | yellow solid, m.p. 94–97° C. | 59.4 | 60.4 | 6.5 | 6.4 | 4.3 | 4.3 |
| 5 | 46140 | trans | —CH₃ | —CH₂CH₂CH₃ | yellow oil | 61.9 | 61.0 | 6.6 | 6.9 | 4.0 | 3.65 |
| 6 | 45748 | trans | —CH₃ | —CH(CH₃)₂ | yellow oil | 61.9 | 63.3 | 6.6 | 6.9 | 4.0 | 5.0 |
| 7 | 46686 | trans | —CH₂CH₃ | —CH(CH₃)₂ | yellow oil | | | | | | |
| 8 | 46716 | trans | —(CH₂)₄CH₃ | —CH(CH₃)₂ | orange oil | | | | | | |
| 9 | 46017 | trans | —CH₃ | —(CH₂)₃CH₃ | yellow oil | 62.8 | 62.3 | 6.9 | 8.7 | 3.85 | 3.9 |
| 10 | 46018 | trans | —CH₃ | —CH₂CH(CH₃)₂ | yellow oil | 62.8 | 61.6 | 6.9 | 9.0 | 3.85 | 3.7 |
| 11 | 45930 | trans | —CH₃ | —CH(CH₃)—CH₂CH₃ | orange oil | 63.0 | | 6.2 | | 3.9 | |
| 12 | 46381 | trans | —CH₃ | —CH(CH₃)—CH₂CH₃ (R) | colorless oil | 63.0 | 63.4 | 6.7 | 6.9 | 3.9 | 3.4 |
| 13 | 46382 | trans | —CH₃ | —CH(CH₃)—CH₂CH₃ (S) | brown oil | 63.0 | | 6.7 | | 3.9 | |
| 14 | 46495 | trans | —CH₃ | —C(CH₃)₃ | yellow solid, m.p. 95–98° C. | 62.8 | 62.6 | 6.9 | 7.42 | 3.85 | 6.45 |
| 15 | 46643 | trans | —CH₃ | —CH₂CF₃ | yellow oil | | | | | | |
| 16 | 46877 | trans | —CH₃ | —CH(CF₃)₂ | yellow oil | | | | | | |
| 18 | 46910 | trans | —CH₃ | —CH₂—C₆H₅ | brown oil | | | | | | |
| 19 | 46246 | trans | —CH₃ | —(CH₂)₂OCH₂CH₃ | yellow oil | | | | | | |
| 20 | 46231 | trans | —CH₃ | cyclopentyl | brown oil | 64.0 | 63.9 | 6.7 | 6.9 | 3.7 | 3.1 |
| 21 | 46142 | trans | —CH₃ | cyclohexyl | yellow oil | | | | | | |
| 22 | 46139 | trans | —CH₃ | 4-isopropyl-1-methylcyclohexyl | yellow oil | 66.5 | 67.3 | 8.1 | 7.7 | 3.2 | 4.3 |

TABLE II

PLANT GROWTH REGULATING ACTIVITY

| Compound No. | | ABI | GSD-MB | GSD-BG | EE | C DEF | C DES | CRInh |
|---|---|---|---|---|---|---|---|---|
| 1 | 46496 | 30 | 100 | 100 | 100 | 0 | 0 | 0 |

TABLE II-continued

PLANT GROWTH REGULATING ACTIVITY

| Compound No. | ABI | GSD-MB | GSD-BG | EE | C DEF | C DES | CRInh |
|---|---|---|---|---|---|---|---|
| 2 46095 | 95 | 100 | 100 | 20 | 0 | 0 | 85 |
| 3 46019 | — | 0[a] | 0[a] | 0 | 50 | 0 | 90 |
| 4 46183 | 0 | 0 | 0 | 44 | 0 | 0 | 0 |
| 5 46140 | 70 | 76[b] | 81[b] | 42 | 50 | 0 | 40 |
| 6 45748 | 99 | 100 | 90 | 24 | 50 | 0 | 96 |
| 7 46686 | 90 | 92[b] | 100[b] | 20 | 0 | 0 | 80 |
| 8 46716 | 70 | 46 | 36 | 0 | 0 | 0 | 0 |
| 9 46017 | 70 | 0[a] | 0[a] | 0 | 50 | 0 | 90 |
| 10 46018 | 95 | 0[a] | 0[a] | 28 | 38 | 0 | 90 |
| 11 45930 | 98 | 100[b] | 100[b] | 0 | 50 | 0 | 96 |
| 12 46381 | 90 | 73[b] | 100[b] | 0 | 0 | 0 | 90 |
| 13 46382 | 95 | 100[b] | 100[b] | 0 | 0 | 0 | 90 |
| 14 46495 | 95 | 85[b] | 92[b] | 79 | 0 | 0 | 40 |
| 15 46643 | 95 | 100[c] | 100[c] | 71 | 50 | 0 | 70 |
| 16 46877 | 90 | 100[b] | 100[b] | 80 | 0 | 0 | 0 |
| 17 46715 | 95 | 92 | 100 | 0 | 0 | 0 | 90 |
| 18 46910 | 95 | 100 | 100[b] | 0 | 0 | 0 | 80 |
| 19 46246 | 80 | 100[b] | 100[b] | 43 | 13 | 0 | 0 |
| 20 46231 | 95 | 92 | 92[b] | 102 | 0 | 0 | 80 |
| 21 46142 | 80 | 100[b] | 77[b] | 23 | 50 | 0 | 50 |
| 22 46139 | 0 | 0 | 35 | 0 | 12 | 0 | 75 |

[a] branching inhibited
[b] show negative geotropism
[c] top growth stunted
ABI = Axillary Bud Inhibition
GSD-MB = Germination and Seedling Development-Mung Bean
GSD-BG = Germination and Seedling Development-Barnyard Grass
EE = Ethylene Evolution
C DEF = Cotton Defoliation
C DES = Cotton Desiccation
CRInh = Cotton Regrowth Inhibition

TABLE III

HERBICIDAL ACTIVITY

| Compound No. | Pre-Emergent | | | | | | | | Post-Emergent | | | | | | | |
|---|---|---|---|---|---|---|---|---|---|---|---|---|---|---|---|---|
| | LQ | MUS | PGW | BG | CG | WO | SB | R | LQ | MUS | PGW | BG | CG | WO | SB | R |
| 1 46496 | 0 | 0 | 0 | 50 | 0 | 0 | 0 | 0 | 0 | 0 | 0 | 0 | 0 | 0 | 30 | 0 |
| 2 46095 | 90 | 90 | 90 | 90 | 90 | 90 | 85 | 90 | 75 | 80 | 80 | 60 | 60 | 60 | 70 | 60 |
| 3 46019 | 90 | 90 | 90 | 90 | 90 | 90 | 90 | 90 | 78 | 78 | 78 | 65 | 55 | 50 | 75 | 50 |
| 4 46183 | 0 | 0 | 0 | 0 | 0 | 0 | 0 | 0 | 0 | 0 | 0 | 0 | 0 | 0 | 0 | 0 |
| 5 46140 | 95 | 93 | 90 | 90 | 90 | 90 | 90 | 90 | 65 | 80 | 80 | 50 | 55 | 50 | 75 | 50 |
| 6 45748 | 94 | 94 | 94 | 94 | 100 | 94 | 94 | 94 | 80 | 80 | 80 | 50 | 50 | 50 | 80 | 50 |
| 7 46686 | 95 | 95 | 95 | 85 | 85 | 90 | 90 | 80 | 80 | 70 | 80 | 80 | 80 | 80 | 70 | 80 |
| 8 46716 | 80 | 70 | 80 | 70 | 70 | 50 | 30 | 50 | 40 | 40 | 60 | 20 | 0 | 30 | 30 | 0 |
| 9 46017 | 90 | 90 | 90 | 85 | 90 | 90 | 85 | 90 | 80 | 80 | 80 | 40 | 35 | 45 | 80 | 35 |
| 10 46018 | 95 | 90 | 90 | 90 | 90 | 90 | 95 | 90 | 78 | 80 | 80 | 60 | 60 | 60 | 88 | 40 |
| 11 45930 | 90 | 90 | 90 | 93 | 93 | 99 | 93 | 99 | 55 | 80 | 75 | 50 | 30 | 50 | 90 | 50 |
| 12 46381 | 80 | 80 | 80 | 80 | 80 | 80 | 80 | 80 | 75 | 75 | 75 | 45 | 35 | 35 | 75 | 35 |
| 13 46382 | 80 | 80 | 80 | 80 | 80 | 80 | 80 | 80 | 70 | 70 | 70 | 50 | 35 | 35 | 70 | 35 |
| 14 46495 | 80 | 80 | 80 | 80 | 80 | 90 | 80 | 70 | 70 | 80 | 60 | 70 | 30 | 40 | 70 | 20 |
| 15 46643 | 95 | 95 | 95 | 90 | 80 | 80 | 90 | 80 | 90 | 80 | 90 | 70 | 70 | 70 | 95 | 70 |
| 16 46877 | 80 | 80 | 80 | 70 | 70 | 80 | 80 | 70 | 80 | 80 | 80 | 0 | 0 | 0 | 80 | 0 |
| 17 46715 | 90 | 90 | 90 | 90 | 90 | 90 | 90 | 90 | 70 | 70 | 70 | 30 | 30 | 30 | 70 | 30 |
| 18 46910 | 80 | 90 | 80 | 70 | 80 | 80 | 80 | 80 | 70 | 70 | 80 | 0 | 0 | 0 | 80 | 0 |
| 19 46246 | 80 | 80 | 80 | 75 | 80 | 75 | 75 | 75 | 45 | 60 | 50 | 0 | 0 | 0 | 65 | 0 |
| 20 46231 | 80 | 80 | 80 | 80 | 80 | 80 | 80 | 80 | 60 | 65 | 60 | 35 | 35 | 35 | 70 | 35 |
| 21 46142 | 90 | 90 | 90 | 80 | 80 | 80 | 90 | 90 | 55 | 70 | 70 | 30 | 30 | 30 | 70 | 30 |
| 22 46139 | 0 | 0 | 0 | 0 | 0 | 0 | 0 | 0 | 0 | 0 | 0 | 0 | 0 | 0 | 25 | 0 |

LQ = Lambsquarter
PGW = Pigweed
CG = Crabgrass
SB = Soybean
MUS = Mustard
BG = Barnyard Grass
WO = Wild Oat
R = Rice

TABLE IV

| Compound No. | Structure |
|---|---|
| 7 (46686) | 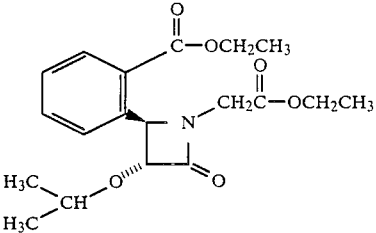 |
| 10C (41736) (covered by U.S. Pat. No. 4,479,900) | 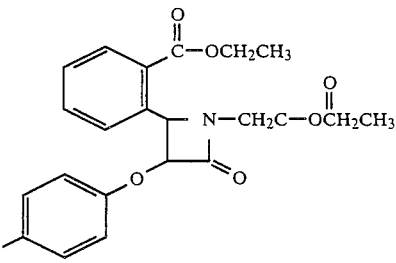 |

TABLE VI (Test From TABLE V)
MEAN SPECIES HEIGHT IN CENTIMETERS

| Compound | Rate microgram/cm$^2$ | Velvet Leaf | Pigweed sp. | Wild Mustard | Soybean |
|---|---|---|---|---|---|
| 7 [46686] | 4.40 | 16 | 2 | — | 28 |
|  | 1.76 | 23 | 3 | — | 39 |
|  | 0.70 | 22 | 3 | — | 44 |
|  | 0.28 | 20 | 4 | — | 51 |
| 10C [41736] | 4.40 | 15 | 4 | — | 12 |
|  | 1.76 | 31 | 3 | — | 13 |
|  | 0.70 | 36 | 4 | — | 20 |
|  | 0.28 | 31 | 4 | — | 26 |
| Check | 0.00 | 15 | 22 | — | 37 |

TABLE VII

POST-EMERGENT HERBICIDAL ACTIVITY (% PHYTOTOXICITY)**

| | Compound No. 7 Rate microgram/cm$^2$ | | | | Chlorflurenol* Rate microgram/cm$^2$ | | |
|---|---|---|---|---|---|---|---|
| | 1.8 | 0.72 | 0.29 | 0.12 | 27.5 | 11.0 | 4.4 |
| BROADLEAF CROPS Soybean | 53 | 20 | 1 | 0 | 80 | 80 | 75 |
| GRASS CROPS Rice | 23 | 13 | 10 | 5 | 8 | 3 | 0 |
| BROADLEAF WEEDS | | | | | | | |
| Redroot Pigweed | 86 | 83 | 76 | 53 | 85 | 83 | 80 |
| Wild Mustard | 76 | 73 | 70 | 51 | 71 | 70 | 70 |
| Lambsquarters | 66 | 55 | 46 | 13 | 55 | 50 | 50 |
| GRASS WEEDS | | | | | | | |
| Wild Oats | 60 | 56 | 40 | 20 | 71 | 60 | 40 |
| Crabgrass | 10 | 0 | 0 | 0 | 15 | 0 | 0 |
| CA Barnyard Grass | 68 | 65 | 53 | 20 | 51 | 30 | 20 |

*Commercial herbicide and plant growth regulator, used for retarding grasses and controlling broadleaf weeds and vines.
**Tests were read after 22 days.

TABLE VIII

POST-EMERGENCE HERBICIDAL ACTIVITY (FOLIAR SPRAY)*

| Compound | Rate | Cheat Grass | Yellow Nutsedge | Ital. Rye Grass | Switch Grass | Yellow Foxtail | Johnson Grass | Prickly Sida | Velvet Leaf | Field Bindweed | Jimson Weed | Sickle Pod |
|---|---|---|---|---|---|---|---|---|---|---|---|---|
| 7 (46686) | 4.40 | 46 | 46 | 50 | 48 | 46 | 36 | 35 | 50 | 76 | 70 | 33 |
|  | 1.76 | 38 | 25 | 33 | 50 | 28 | 0 | 16 | 30 | 65 | 58 | 18 |
|  | 0.70 | 35 | 13 | 11 | 30 | 20 | 0 | 15 | 23 | 68 | 50 | 15 |
|  | 0.28 | 20 | 1 | 0 | 10 | 0 | 0 | 10 | 10 | 41 | 30 | 10 |
| 10C (41736) | 4.40 | 23 | 0 | 0 | 10 | 10 | 0 | 10 | 56 | 66 | 66 | 20 |
|  | 1.76 | 11 | 0 | 0 | 0 | 0 | 0 | 10 | 43 | 50 | 36 | 10 |
|  | 0.70 | 0 | 0 | 0 | 0 | 0 | 0 | 10 | 23 | 50 | 35 | 0 |
|  | 0.28 | 0 | 0 | 0 | 0 | 0 | 0 | 5 | 0 | 25 | 13 | 0 |
| 2,4-D | 4.40 | 30 | 45 | 0 | 71 | 20 | 33 | 88 | 75 | 100 | 70 | 75 |
|  | 1.76 | 3 | 23 | 0 | 36 | 0 | 16 | 81 | 73 | 90 | 61 | 70 |
|  | 0.70 | 0 | 10 | 0 | 0 | 0 | 70 | 50 | 40 | 50 | 43 | |
|  | 0.28 | 0 | 0 | 0 | 0 | 0 | 63 | 15 | 20 | 36 | 20 | |
| Check | 0.0 | 0 | 0 | 0 | 0 | 0 | 0 | 0 | 0 | 0 | 0 | 0 |

| Compound | Rate | Peanuts | Sugar Beets | Cotton | Tomato | Alfalfa | Peas | Oats | Sorgum (NK125) | Anza Wheat | Field Corn |
|---|---|---|---|---|---|---|---|---|---|---|---|
| 7 (46686) | 4.40 | 38 | 70 | 50 | 73 | 10 | 1 | 53 | 15 | 46 | 10 |
|  | 1.76 | 20 | 60 | 35 | 65 | 3 | 0 | 51 | 10 | 38 | 0 |
|  | 0.70 | 0 | 50 | 20 | 58 | 0 | 0 | 41 | 0 | 26 | 0 |
|  | 0.28 | 0 | 40 | 10 | 45 | 0 | 0 | 35 | 0 | 18 | 0 |
| 10C (41736) | 4.40 | 13 | 61 | 56 | 50 | 11 | 8 | 51 | 3 | 15 | 1 |
|  | 1.76 | 3 | 58 | 40 | 40 | 0 | 0 | 30 | 0 | 10 | 0 |
|  | 0.70 | 0 | 50 | 35 | 35 | 0 | 0 | 23 | 0 | 6 | 0 |
|  | 0.28 | 0 | 40 | 15 | 15 | 0 | 20 | 0 | 5 | 0 | |
| 2,4-D | 4.40 | 36 | 100 | 85 | 99 | 99 | 100 | 10 | 33 | 10 | 18 |
|  | 1.76 | 26 | 97 | 78 | 97 | 90 | 70 | 0 | 16 | 5 | 10 |
|  | 0.70 | 16 | 89 | 60 | 89 | 58 | 23 | 0 | 3 | 1 | 1 |
|  | 0.28 | 13 | 86 | 56 | 86 | 11 | 10 | 0 | 0 | 1 | 0 |

*Tests were read after three weeks.

TABLE VI (Test From TABLE V)
MEAN SPECIES HEIGHT IN CENTIMETERS

| Compound | Rate microgram/cm$^2$ | Velvet Leaf | Pigweed sp. | Wild Mustard | Soybean |
|---|---|---|---|---|---|
| 7 [46686] | 4.40 | 16 | 2 | — | 28 |
|  | 1.76 | 23 | 3 | — | 39 |

TABLE V

POST-EMERGENCE HERBICIDAL ACTIVITY (% PHYTOTOXICITY)

| | Compound No. 7 Rate microgram/cm$^2$ | | | | [2,4-D] Rate microgram/cm$^2$ | | | | Compound 10C Rate microgram/cm$^2$ | | | |
|---|---|---|---|---|---|---|---|---|---|---|---|---|
| | 4.4 | 1.76 | 0.70 | 0.28 | 4.4 | 1.76 | 0.70 | 0.28 | 4.4 | 1.76 | 0.70 | 0.28 |
| 1st Reading (20 Days) | | | | | | | | | | | | |
| BROADLEAF CROPS | | | | | | | | | | | | |
| Soybean | 43 | 23 | 6 | 0 | 88 | 78 | 63 | 46 | 85 | 85 | 78 | 63 |
| BROADLEAF WEEDS | | | | | | | | | | | | |
| Velvet leaf | 50 | 23 | 25 | 20 | 60 | 46 | 46 | 26 | 40 | 30 | 13 | 0 |
| Pigweed Sp. | 95 | 95 | 95 | 91 | 91 | 90 | 73 | 56 | 80 | 80 | 80 | 71 |
| Wild Mustard | 80 | 80 | 78 | 78 | 98 | 91 | 86 | 73 | 71 | 70 | 85 | 60 |
| 2nd Reading (40 days) | | | | | | | | | | | | |
| BROADLEAF CROPS | | | | | | | | | | | | |
| Soybean | 35 | 10 | 0 | 0 | — | — | — | — | 78 | 75 | 41 | 16 |
| BROADLEAF WEEDS | | | | | | | | | | | | |
| Velvet leaf | 26 | 0 | 0 | 0 | — | — | — | — | 33 | 0 | 0 | 0 |
| Pigweed sp. | 83 | 83 | 78 | 75 | — | — | — | — | 75 | 68 | 70 | 65 |
| Wild Mustard | 98 | 100 | 100 | 91 | — | — | — | — | 100 | 100 | 100 | 100 |

TABLE IX

PRE-EMERGENCE HERBICIDAL ACTIVITY IN SANDY CLAY LOAM*

| Compound | Rate microgram/cm$^2$ | Wild Oats | Crab Grass | CA Barnyard Grass | Velvet Leaf | Redroot Pigweed | Wild Mustard | Rice | Soybean |
|---|---|---|---|---|---|---|---|---|---|
| 7 (46686) | 4.40 | 78 | 85 | 90 | 71 | 98 | 98 | 81 | 56 |
| | 1.76 | 73 | 83 | 85 | 46 | 98 | 95 | 80 | 50 |
| | 0.70 | 56 | 50 | 65 | 13 | 96 | 95 | 60 | 40 |
| | 0.28 | 23 | 23 | 46 | 0 | 68 | 86 | 40 | 13 |
| 10C (41736) | 4.40 | 46 | 46 | 30 | 66 | 98 | 93 | 71 | 75 |
| | 1.76 | 40 | 23 | 10 | 10 | 95 | 88 | 48 | 61 |
| | 0.70 | 20 | 0 | 0 | 0 | 53 | 70 | 20 | 33 |
| | 0.28 | 10 | 0 | 0 | 0 | 6 | 0 | 10 | 6 |
| 2,4-D | 4.40 | 53 | 90 | 85 | 100 | 98 | 100 | 93 | 92 |
| | 1.76 | 10 | 10 | 63 | 78 | 78 | 93 | 63 | 43 |
| | 0.70 | 0 | 0 | 20 | 21 | 75 | 89 | 48 | 10 |
| | 0.28 | 0 | 0 | 0 | 0 | 16 | 92 | 23 | 0 |
| Check | 0.0 | 0 | 0 | 0 | 0 | 0 | 0 | 0 | 0 |

*Tests were read at 31 days.

TABLE X

PHYTOTOXICITY (%) AFTER 20 DAYS OF SPRAYING (POST-EMERGENCE APPLICATION)

| Compound | Rate Kg A.I/HA | Soybeans | Cotton | Corn | Rice | B. Decumbers | Alexander Grass | Jungle Rice | Wild Poinsetta | C. M. Glory | Arrowleaf Sida |
|---|---|---|---|---|---|---|---|---|---|---|---|
| 7 (46686) | 1.0 | 70 | 30 | 0 | 0 | 0 | 60 | 50 | 40 | 80 | 15 |
| | 0.5 | 60 | 20 | 0 | 0 | 0 | 50 | 40 | 30 | 80 | 10 |
| | 0.25 | 40 | 10 | 0 | 0 | 0 | 40 | 10 | 10 | 80 | 5 |
| | 0.125 | 25 | 5 | 0 | 0 | 0 | 15 | 10 | 5 | 80 | 0 |
| | 0.062 | 20 | 3 | 0 | 0 | 0 | 0 | 5 | 0 | 70 | 0 |
| 10C (41736) | 1.0 | 80 | 80 | 0 | 20 | 10 | 20 | 0 | 20 | 60 | 30 |
| | 0.5 | 80 | 60 | 0 | 5 | 0 | 0 | 0 | 10 | 50 | 30 |
| | 0.25 | 80 | 30 | 0 | 0 | 0 | 0 | 0 | 5 | 20 | 10 |
| | 0.125 | 50 | 10 | 0 | 0 | 0 | 0 | 0 | 0 | 10 | 5 |
| | 0.062 | 45 | 0 | 0 | 0 | 0 | 0 | 0 | 0 | 5 | 0 |

TABLE XI

MEAN HEIGHT 25 DAYS AFTER POST-EMERGENCE TREATMENT (in cm)

| Compound | Rate KgA.I/HA | Soybeans | Cotton | Morning Glory |
|---|---|---|---|---|
| 7 (46686) | 1.0 | 30.4 | 39.7 | 4.8 |
| | 0.5 | 31.8 | 43.0 | 6.6 |
| | 0.25 | 34.6 | 44.8 | 7.2 |
| | 0.125 | 36.4 | 45.8 | 8.2 |
| | 0.062 | 35.2 | 49.8 | 6.0 |
| 10C (41736) | 1.0 | 14.6 | 20.2 | 16.8 |
| | 0.5 | 13.4 | 22.2 | 19.4 |
| | 0.25 | 15.4 | 36.4 | 24.0 |
| | 0.125 | 14.8 | 42.2 | 40.6 |
| | 0.062 | 19.8 | 52.6 | 36.7 |
| Check | — | 51.8 | 48.5 | 59.3 |

TABLE XII

POTATO SPROUT INHIBITION**

| Compound | Concentration (ppm) | Number of Non-infected Eyes | Number of Sprouted Eyes | % of Buds Sprouted | M Length Sprouted Buds | % of Check |
|---|---|---|---|---|---|---|
| 7 [46686] | 900 | 13 | 13 | 100 | 8.84 | 15.6 |
|  | 300 | 18 | 17 | 94 | 14.94 | 26.4 |
|  | 100 | 20 | 20 | 100 | 17.10 | 30.2 |
| IAA* | 900 | 16 | 14 | 88 | 20.67 | 36.5 |
|  | 300 | 19 | 19 | 100 | 30.05 | 53.1 |
|  | 100 | 16 | 16 | 100 | 36.75 | 65.0 |
| Check | — | 18 | 16 | 89 | 56.56 | 100 |

*IAA = Indole-3-Acetic Acid, an auxin-type plant growth regulator.
**Read at 20 days.

EXAMPLE K

Field Test on Soybean Yield

Compounds were tested for their effects on soybean yield under field conditions.

The test formulation was uniformly sprayed on small plots with two replicates. Soybeans (glycine max) were planted June 16. On July 29, the plots were sprayed using a tractor boom spray. At the time of spraying, the soybeans were about 18 to 24 inches in height. The rates of 0.500, 0.375, 0.280, 0.210 and 0.160 Kg/ha were applied in 234 L/Ha spray in a foliar spray. Soybean yield was measured November 27 (after about 4 months) in bushels per acre.

TABLE XIII

Field Test on Soybean Yield

| Compound | Application Rate (Kg/Ha) | Yield (Bushels/Acre) |
|---|---|---|
| 7 (RE 46686) | 0.500 | 24.26 |
|  | 0.375 | 19.49 |
|  | 0.280 | 18.52 |
|  | 0.210 | 18.47 |
|  | 0.160 | 17.44 |
| 10C (RE 41736) | 0.500 | 16.91 |
|  | 0.375 | 19.39 |
|  | 0.280 | 24.66 |
|  | 0.210 | 20.29 |
|  | 0.160 | 17.37 |
| UTC* | 0.00 | 22.42 |

*Untreated Check

What is claimed is:

1. A compound of the formula:

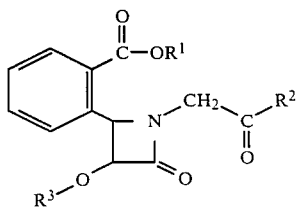

wherein $R^1$ is lower alkyl of 1 to 6 carbon atoms lower alkenyl of 2 to 6 carbon atoms or benzyl; $R^2$ is lower alkoxy of 1 to 6 carbon atoms, benzyloxy or the group

wherein $R^4$ is lower alkoxy of 1 to 4 carbon atoms; and $R^3$ is hydrogen, lower alkyl of 1 to 6 carbon atoms, lower alkyl of 1 to 6 carbon atoms substituted with 1 to 3 trihalomethyl groups, lower haloalkyl of 1 to 6 carbon atoms substituted with 1 to 6 halogen atoms, lower alkenyl of 2 to 6 carbon atoms, arylalkyl of 7 to 12 carbon atoms, lower alkoxyalkyl of 2 to 6 carbon atoms, lower alkylthioalkyl of 2 to 6 carbon atoms, or lower cycloalkyl of 3 to 8 carbon atoms.

2. A compound according to claim 1 wherein the compound is the trans isomer.

3. A compound according to claim 1 wherein $R^3$ is lower alkyl, lower haloalkyl or lower alkyl substituted with 1 to 3 trihalomethyl groups.

4. A compound according to claim 3 wherein $R^3$ is $\beta,\beta,\beta$-trifluoroethyl, isopropyl or tert-butyl.

5. A compound according to claim 4 wherein the compound is the trans isomer.

6. A compound according to claim 3 wherein $R^2$ is lower alkoxy.

7. A compound according to claim 6 wherein $R^1$ is methyl or ethyl.

8. A compound according to claim 7 wherein $R^2$ is ethoxy.

9. A compound according to claim 8 wherein $R^3$ is $\beta,\beta,\beta$-trifluoroethyl, isopropyl or tert-butyl.

10. A compound according to claim 9 wherein $R^1$ is methyl.

11. A compound according to claim 10 wherein $R^3$ is $\beta,\beta,\beta$-trifluoroethyl.

12. A compound according to claim 11 wherein the compound is the trans isomer.

13. A compound according to claim 10 wherein $R^3$ is isoproypyl.

14. A compound according to claim 13 wherein the compound is the trans isomer.

15. A compound according to claim 10 wherein $R^3$ is tert-butyl.

16. A compound according to claim 15 wherein the compound is the trans isomer.

17. A compound according to claim 1 wherein $R^1$ is ethyl and $R^3$ is isopropyl.

18. A compound according to claim 17 wherein the compound is the trans isomer.

19. A compound according to claim 17 wherein $R^2$ is lower alkoxy.

20. A compound according to claim 19 wherein $R^2$ is ethoxy.

21. A compound according to claim 20 wherein the compound is the trans isomer.

22. A plant growth regulating composition comprising a biologically inert carrier and a plant growth regulating effective amount of a compound of the formula:

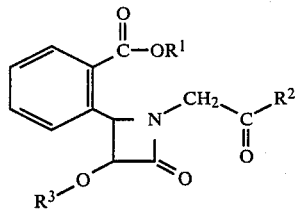

wherein $R^1$ is lower alkyl of 1 to 6 carbon atoms lower alkenyl of 2 to 6 carbon atoms or benzyl; $R^2$ is lower alkoxy of 1 to 6 carbon atoms, benzyloxy or the group

where $R^4$ is lower alkoxy of 1 to 4 carbon atoms; and $R^3$ is hydrogen, lower alkyl of 1 to 6 carbon atoms, lower alkyl of 1 to 6 carbon atoms substituted with 1 to 3 trihalomethyl groups, lower haloalkyl of 1 to 6 carbon atoms substituted with 1 to 6 halogen atoms, lower alkenyl of 2 to 6 carbon atoms, arylalkyl of 7 to 12 carbon atoms, lower alkoxyalkyl of 2 to 6 carbon atoms, lower alkylthioalkyl of 2 to 6 carbon atoms, or lower cycloalkyl of 3 to 8 carbon atoms.

23. A plant growth regulating composition in accordance with claim 22 wherein the compound is the trans isomer.

24. A plant growth regulating composition in accordance with claim 22 wherein $R^3$ is $\beta,\beta,\beta$-trifluoroethyl, isopropyl or tert-butyl.

25. A plant growth regulating composition in accordance with claim 22 wherein $R^1$ is methyl, $R^2$ is ethoxy and $R^3$ is $\beta,\beta,\beta$-trifluoroethyl.

26. A plant growth regulating composition in accordance with claim 22 wherein $R^2$ is ethoxy and $R^3$ is isopropyl.

27. A plant growth regulating composition in accordance with claim 26 wherein $R^1$ is methyl.

28. A plant growth regulating composition in accordance with claim 26 wherein $R^1$ is ethyl.

29. A plant growth regulating composition in accordance with claim 22 wherein $R^1$ is methyl, $R^2$ is ethoxy and $R^3$ is tert-butyl.

30. A method for regulating the growth of vegetation which comprises applying to said vegetation or its habitat a plant growth regulating effective amount of a compound of the formula:

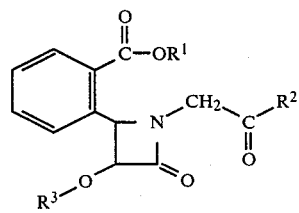

wherein $R^1$ is lower alkyl of 1 to 6 carbon atoms lower alkenyl of 2 to 6 carbon atoms or benzyl; $R^2$ is lower alkoxy of 1 to 6 carbon atoms, benzyloxy or the group

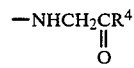

where $R^4$ is lower alkoxy of 1 to 4 carbon atoms; and $R^3$ is hydrogen, lower allkyl of 1 to 6 carbon atoms, lower alkyl of 1 to 6 carbon atoms substituted with 1 to 3 trihalomethyl groups, lower haloalkyl of 1 to 6 carbon atoms substituted with 1 to 6 halogen atoms, lower alkenyl of 2 to 6 carbon atoms, arylalkyl of 7 to 12 carbon atoms, lower alkoxyalkyl of 2 to 6 carbon atoms, lower alkylthioalkyl of 2 to 6 carbon atoms, or lower cycloalkyl of 3 to 8 carbon atoms.

31. The method in accordance with claim 30 wherein the compound is the trans isomer.

32. The method in accordance with claim 30 wherein $R^3$ is $\beta,\beta,\beta$-trifluoroethyl, isopropyl or tert-butyl.

33. The method in accordance with claim 30 wherein $R^2$ is ethoxy and $R^3$ is isopropyl.

34. The method in accordance with claim 33 wherein $R^1$ is methyl.

35. The method in accordance with claim 33 wherein $R^1$ is ethyl.

36. The method in accordance with claim 30 wherein $R^1$ is methyl, $R^2$ is ethoxy and $R^3$ is tert-butyl.

37. A method of controlling undesired vegetation which comprises supplying a herbicidally effective amount of a compound of claim 17, or mixtures thereof, to the foliage and/or growth medium of said plants.

38. A method of controlling undesired vegetation which comprises supplying a herbicidally effective amount of a compound of claim 18, or mixtures thereof, to the foliage and/or growth medium of said plants.

39. A method of controlling undesired vegetation which comprises supplying a herbicidally effective amount of a compound of claim 20, or mixtures thereof, to the foliage and/or growth medium of said plants.

40. A method of combatting weeds in a crop locus which comprises applying to said locus a selective herbcidally effective amount of a compound of claim 17, or mixtures thereof.

41. A method of combatting weeds in a crop locus which comprises applying to said locus a selective herbicidally effective amount of a compound of claim 18, or mixtures thereof.

42. A method of combatting weeds in a crop locus which comprises applying to said locus a selective herbcidally effective amount of a compound of claim 20, or mixtures thereof.

43. A method of for selectively controlling weeds in crops which comprises applying to said crops, after emergence thereof, a weed-controlling effective amount of a compound of claim 17, or mixtures thereof.

44. A method of for selectively controlling weeds in crops which comprises applying to said crops, after emergence thereof, a weed-controlling effective amount of a compound of claim 20, or mixtures thereof.

45. The method according to claim 44 wherein said crops are soybeans, cotton, alfalfa, peas sorgun or corn.

46. A method of selectively controlling weeds in soybean fields which comprises applying post-emergently to the plants in said fields an effective amount sufficient to control weeds, but insufficient to cause substantial permanent injury to soybeans of a compound of claim 17, or mixtures thereof.

47. A method of selectively controlling weeds in soybean fields which comprises applying post-emergently to the plants in said fields an effective amount sufficient to control weeds, but insufficient to cause substantial permanent injury to soybeans of a compound of claim 20, or mixtures thereof.

48. A herbicidal composition comprising a herbicidally effective amount of a compound of claim 17, or mixtures thereof, and a compatible carrier.

49. A herbicidal composition comprising a herbcidally effective amount of a compound of claim 18, or mixtures thereof, and a compatible carrier.

50. A herbicidal composition comprising a herbicidally effective amount of a compound of claim 20, or mixtures thereof, and a compatible carrier.

51. A composition for selectively controlling the growth of weeds in areas having crops therein comprising a selective herbicidally effective amount of a compound of claim 17, or mixtures thereof, and a compatible carrier.

52. A composition for selectively controlling the growth of weeds in areas having crops therein comprising a selective herbicidally effective amount of a compound of claim 20, or mixtures thereof, and a compatible carrier.

53. A method of regulating the growth of plants to obtain an increase in yield which comprises applying thereto a yield enhancing effective amount of a compound of claim 1 to said plants or the locus thereof.

54. The method of claim 53 wherein said plants are soybeans or broadleaf seed and oil crop plants.

55. The method of claim 53 wherein said plants are soybeans.

56. A method of regulating the growth of plants to obtain an increase in yield which comprises applying thereto a yield enhancing effective amount of a compound of claim 4 to said plants or the locus thereof.

57. A method of regulating the growth of plants to obtain an increase in yield which comprises applying thereto a yield enhancing effective amount of a compound of claim 17 to said plants or the locus thereof.

58. A method of regulating the growth of plants to obtain an increase in yield which comprises applying thereto a yield enhancing effective amount of a compound of claim 20 to said plants or the locus thereof.

59. The method of claim 58 wherein said plants comprises soybeans or broadleaf seed and oil crop plants.

60. The method of claim 58 wherein said plants comprise soybeans.

* * * * *